US008735512B2

(12) United States Patent
Walker et al.

(10) Patent No.: US 8,735,512 B2
(45) Date of Patent: May 27, 2014

(54) CURING AGENT FOR LOW TEMPERATURE CURE APPLICATIONS

(75) Inventors: Frederick Herbert Walker, Allentown, PA (US); Michael Ian Cook, De Meern (NL); Gamini Ananda Vedage, Bethlehem, PA (US); Robert Marjo Theodoor Rasing, Didam (NL)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 12/100,096

(22) Filed: Apr. 9, 2008

(65) Prior Publication Data

US 2009/0259003 A1 Oct. 15, 2009

(51) Int. Cl.
| | |
|---|---|
| C08F 283/00 | (2006.01) |
| C09K 3/00 | (2006.01) |
| C08G 59/14 | (2006.01) |
| C08L 63/00 | (2006.01) |
| C08G 73/02 | (2006.01) |
| C07C 209/00 | (2006.01) |

(52) U.S. Cl.
USPC ...... 525/534; 252/182.13; 525/523; 525/540; 564/280

(58) Field of Classification Search
CPC ...... C08G 14/06; C08G 14/14; C08G 59/504; C08G 59/56; C08L 63/00
USPC .......................................... 525/523; 523/523
See application file for complete search history.

(56) References Cited

U.S. PATENT DOCUMENTS

| | | | | |
|---|---|---|---|---|
| 3,654,370 | A | | 4/1972 | Yeakey |
| 4,162,358 | A | * | 7/1979 | Marquis et al. ............... 528/120 |
| 4,269,742 | A | | 5/1981 | Goeke et al. |
| 5,101,060 | A | * | 3/1992 | Speranza et al. ............. 558/390 |
| 5,280,091 | A | | 1/1994 | Dubowik et al. |
| 5,618,905 | A | | 4/1997 | Marsella et al. |
| 7,666,954 | B2 | | 2/2010 | Walker et al. |
| 2004/0210011 | A1 | * | 10/2004 | Echigo et al. ................. 525/526 |
| 2005/0176899 | A1 | * | 8/2005 | Volle ............................. 525/525 |
| 2011/0065958 | A1 | | 3/2011 | Abdourazak et al. |

FOREIGN PATENT DOCUMENTS

| | | |
|---|---|---|
| DE | 122258 A | 9/1976 |
| DE | 130580 A | 4/1978 |
| DE | 28 53 752 A | 10/1979 |
| DE | 38 03 508 C2 | 4/1994 |
| EP | 0 487 188 A1 | 5/1992 |
| GB | 1158076 | 7/1969 |
| GB | 1158076 A * | 7/1969 ............... C08G 9/04 |
| JP | 49-34997 A | 3/1974 |
| JP | 2-103221 A | 4/1990 |
| JP | 09-048852 | 2/1997 |
| JP | 2007-45862 A | 2/2007 |
| JP | 2008-156605 | 7/2008 |
| JP | 2011-057675 | 3/2011 |

OTHER PUBLICATIONS

March, J.; "Advanced Organic Chemistry: Reactions, Mechanisms, and Structure"; Third Edition; Jon Wiley and Sons, New York; 1985; pp. 496, 800-802.
Marsella, J., et al; "Acceleration of Amine/Epoxy Reactions with N-Methyl Secondary Amines"; Journal of Polymer Science; 2000; vol. 38; pp. 921-930.
Williams, J.; "The Beta Relaxation in Epoxy Resin-Based Networks"; Journal of Applied Polymer Science; 1979; vol. 23; pp. 3433-3444.
Matejka, L.; "Amine Cured Epoxide Networks: Formation, Structure, and Properties"; Macromolecules; 2000; vol. 33; pp. 3611-3619.
Sandreczki, T.C., et al; "Electron Paramagnetic Resonance Studies of Amine-Cured Epoxy Resins: Dependence of Nitroxide Spin-Probe Mobility on Cross-Link Density, Free Volume, and Temperature"; Macromolecules; 1984; vol. 17; pp. 1789-1794.
Brown, I.M., et al; "Motional Correlation Times of Nitroxide Spin Labels and Spin Probes in an Amine-Cured Epoxy Resin: Solvent Dependence"; Macromolecules; 1985; vol. 18; pp. 2702-2709.
Jean, Y.C.; "Positronium Annihilation in Amine-Cured Epoxy Polymers"; Journal of Polymer Science; 1986; vol. 24; pp. 1247-1258.
U.S. Appl. No. 11/584,388, filed Oct. 20, 2006.
Solomons, T.W.; "Basicity of Amines: Amine Salts"; Organic Chemistry, Second Edition; pp. 810-813, 1980.
Tanaka, Y.; "Synthesis and Characteristics of Epoxides"; C.A. May, ed.; Epoxy Resins Chemistry and Technology; 1988.

* cited by examiner

*Primary Examiner* — Peter F Godenschwager
*Assistant Examiner* — David Karst
(74) *Attorney, Agent, or Firm* — Michael K. Boyer

(57) ABSTRACT

The present invention provides Mannich base derivatives of N,N'-dimethyl secondary diamine polymers including Mannich base derivatives of methylamine-terminated poly-(N-methylazetidine) and Mannich base derivatives of methylamine-terminated poly-(N-methylazacycloheptane). Amine curing agent compositions and amine-epoxy compositions containing Mannich base derivatives of N,N'-dimethyl secondary diamine polymers are also disclosed.

22 Claims, No Drawings

CURING AGENT FOR LOW TEMPERATURE CURE APPLICATIONS

BACKGROUND OF THE INVENTION

The present invention relates generally to Mannich base derivatives of N,N'-dimethyl secondary diamine polymeric compounds, amine and amine-epoxy compositions employing these materials, and methods of making epoxy resin compositions.

Epoxy resins which are cured, hardened, or crosslinked with multifunctional amines, i.e., amine compounds having three or more active amine hydrogens, are well known in the industry. These materials are widely used in applications such as coatings, adhesives, composites, and civil engineering applications such as formulations for flooring. In coating applications, amine-cured epoxy formulations generally can be cured at room temperature to yield films with high mechanical strength, good water, chemical, and corrosion resistance, and excellent adhesion properties, particularly to metallic substrates. Thus, they are often employed as primers and topcoats for large structures such as ships, bridges, and industrial plants and equipment.

Before regulations placing limits on the volatile organic compound (VOC) content of amine-epoxy coatings, formulations were often based on solid epoxy resins. These resins are solid at room temperature. Coatings using solid epoxy resins usually dried very quickly, since only solvent evaporation, not chemical cure, was required for the coating to reach a dry-to-touch state.

Due to the VOC regulations, epoxy resins that are liquids at room temperature have replaced solid epoxy resins in many applications. This transition has resulted in several problems, for example, in coating applications. Amine-epoxy compositions based upon liquid epoxy resins tend to cure much more slowly than a comparable solid epoxy resin formulation, and this problem becomes more severe at lower temperatures. Shipyards, for example, often reside in locations with cold winters, and paint must be applied when temperatures are about 5° C. or colder. Certain amine-epoxy coating formulations cure very slowly at these temperatures, often requiring at least 24 hours, and in some cases much more than 24 hours, to reach the "walk-on" dry state required so that painters can apply a second or third coat, if required. In the laboratory, the "walk-on" dry state is often estimated by the thumb-twist test method. Slow drying times can dramatically impact a shipyard's productivity. Thus, fast cure speed at below room temperature is a desirable property in many applications.

It is also beneficial to limit the volatility of the amine component in the amine-epoxy formulation. In addition to meeting VOC regulations, reducing volatility can reduce worker exposure and safety concerns.

Amine-epoxy coating formulations based on a liquid epoxy resin, as opposed to a solid epoxy resin, can also be less flexible than required for certain applications. For example, in ships employing modern double hull construction, the steel used in the two hulls that form the ballast tank is a thinner gauge than used in single hull ships. As a result of the thinner gauge, the steel flexes more which can lead to a stress crack failure of the coating, especially around welded joints. This in turn can lead to corrosion, which can be expensive to repair and can affect the ship's integrity. Further, in the rail car industry, there are also problems due to lack of coating flexibility at the weld seams. Additionally, coatings in many other applications require greater flexibility, for example, to achieve a desired impact resistance for a given application, or to post-form a metal after painting. In the end-use application, the amount of stress or deformation that the material undergoes, as well as the rate of deformation, are important factors for determining the flexibility required and thus the suitability of a particular amine-epoxy composition or formulation. In civil engineering applications, for example, those involving concrete and other cementitious materials, amine-epoxy materials capable of withstanding greater expansion and contraction stresses, and capable of meeting crack bridging requirements, are also of interest.

Many epoxy coatings are over-coated with a second or third coating. The additional coatings are not limited to epoxy-based systems and can include other chemical coating systems (e.g., polyurethanes) in order to provide particular end-use properties, such as corrosion resistance, weatherability, etc. Intercoat adhesion in formulations based on liquid epoxy resins typically is less than comparable solid epoxy resin formulations, often leading to intercoat adhesion failures. When adequate intercoat adhesion for a liquid epoxy system is obtained, re-coating often must occur within a limited time frame if intercoat adhesion failures are to be avoided. This time is often referred to as the re-coat window.

Many amine-epoxy coatings suffer from problems referred to in the industry as blush, carbamation, and exudate. These problems, in part, are due to the incompatibility of the amine curing agent and the epoxy resin, which causes phase separation and results in amine migration to the coating surface. In primary amines, the migratory amine can react with $CO_2$ present in the air, resulting in carbamation. Whether in the form of carbamation or the greasy surface layer referred to as exudate or blush, these surface defects detract from the appearance of the coating, and can lead to intercoat adhesion failures if the film is re-coated. These problems are generally worse for coatings applied and cured at colder temperatures, where amine-epoxy compatibility is reduced.

Certain Mannich bases can be used in amine-epoxy formulations because they often exhibit fast cure rates at low temperatures, but such materials are not without drawbacks. For example, amine-epoxy coatings employing certain Mannich bases often suffer from blush, carbamation, and exudate, as well as poor coating flexibility. In addition, depending upon the process used to synthesize the Mannich base compound, unacceptable amounts of residual phenol may remain. Phenol is a toxic chemical, and its presence at levels greater than 1% in a chemical mixture can require special disposal techniques, special labeling, and the use of personal protective equipment to minimize worker exposure.

There are several broad classes of multifunctional amine curing agents that are employed in the amine-epoxy coating industry, including polyamides, Mannich bases (including phenalkamines), and amine adducts. None of these known products addresses the needs or solves the problems noted above. Accordingly, it is to this end that the present invention is directed.

BRIEF SUMMARY OF THE INVENTION

The present invention discloses novel Mannich base derivative compositions comprising Mannich base compounds, and methods of making these new compositions. These Mannich base derivative compositions can be used, for example, as amine-based curing agents in amine-epoxy compositions.

In one aspect of the present invention, the Mannich base derivative composition comprises a Mannich base reaction product of:
  (a) at least one aldehyde compound;
  (b) at least one phenol compound; and (c) at least one N,N'-dimethyl secondary diamine polymer having a number-average molecular weight ($M_n$) from about 140 to about 1000.

In another aspect, the Mannich base derivative composition comprises a reaction product of:
(a) at least one di-substituted or tri-substituted Mannich base compound; and
(b) at least one N,N'-dimethyl secondary diamine polymer having a $M_n$ from about 140 to about 1000.

In yet another aspect, the Mannich base derivative composition comprises amine compounds having the following formula:

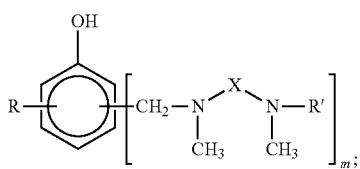
(I-A)

wherein:
m is 1, 2, or 3;
R is a hydrogen atom or a $C_1$-$C_{18}$ linear or branched alkyl or alkenyl group;
each R' independently is a hydrogen atom or a moiety having the formula:

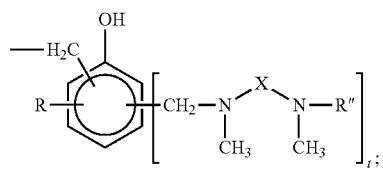
(I-B)

wherein:
R is defined as above;
t is 0, 1, or 2;
each R" independently is a hydrogen atom or a moiety having the formula;

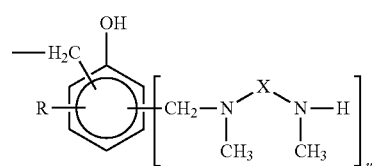
(I-C)

wherein:
R is defined as above;
u is 0, 1, or 2; and
each X independently is a polyoxyalkylene moiety or a moiety having the formula:

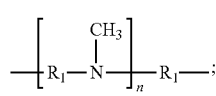
(II)

wherein:
$R_1$ is a $C_2$-$C_8$ linear or branched alkanediyl; and
n is an integer in a range from 0 to 50, inclusive.

Amine curing agent compositions are provided in other aspects of the present invention. Such compositions can be used to cure, harden, or crosslink an epoxy resin. An amine curing agent composition can comprise (i) any one of the three aforementioned Mannich base derivative compositions, provided immediately above; and (ii) at least one multifunctional amine having 3 or more active amine hydrogens.

In another aspect, the present invention is directed to amine-epoxy compositions comprising (a) a Mannich base derivative composition and, optionally, at least one multifunctional amine having 3 or more active amine hydrogens; and (b) an epoxy component comprising at least one multifunctional epoxy resin. Compositions obtained by curing the amine-epoxy compositions of the present invention, as well as articles of manufacture comprising these compositions, are also contemplated by the present invention. Such articles can include, but are not limiting to, a coating, an adhesive, a construction product, a flooring product, a composite product, and the like.

Amine-epoxy compositions of the present invention can be used to produce coatings with improved "walk-on" dry times, rapid hardness development, good gloss and surface appearance, and/or outstanding impact resistance and flexibility as compared to conventional amine-epoxy coatings.

DEFINITIONS

The following definitions and abbreviations are provided in order to aid those skilled in the art in understanding the detailed description of the present invention.
AHEW—amine hydrogen equivalent weight.
BA—benzyl alcohol, commercially available from Fisher Scientific UK Ltd.
CX-105—Sunmide® CX-105, commercially available from Air Products and Chemicals, Inc., phenalkamine, AHEW=142.
DGEBA—diglycidyl ether of bisphenol-A.
EEW—epoxy equivalent weight.
K54—Ancamine® K54, commercially available from Air Products and Chemicals, Inc., tris-(dimethylaminomethyl)phenol.
$M_n$—number-average molecular weight.
MPCA—also abbreviated as MBPCAA. MPCA is a mixture of methylene bridged poly(cyclohexyl-aromatic) amines that fits within the class of multifunctional amines. Ancamine® 2168, commercially available from Air Products and Chemicals, Inc., is a MPCA with an AHEW of 57 and is the grade utilized in the examples.
NC541 LV—Cardolite® NC541 LV, commercially available from Cardolite Corporation, low viscosity phenalkamine, AHEW=125.
PHR—parts per hundred weight resin.

DETAILED DESCRIPTION OF THE INVENTION

Amine and Amine-Epoxy Compositions

The present invention discloses novel Mannich base derivative compositions comprising Mannich base compounds, and methods of making these new compositions. According to one aspect of this invention, the Mannich base derivative composition comprises a Mannich base reaction product of:
(a) at least one aldehyde compound;
(b) at least one phenol compound; and (c) at least one N,N'-dimethyl secondary diamine polymer having a number-average molecular weight ($M_n$) from about 140 to about 1000.

In another aspect, the Mannich base derivative composition comprises a reaction product of:

(a) at least one di-substituted or tri-substituted Mannich base compound; and (b) at least one N,N'-dimethyl secondary diamine polymer having a $M_n$ from about 140 to about 1000.

In yet another aspect, the Mannich base derivative composition comprises amine compounds having the following formula:

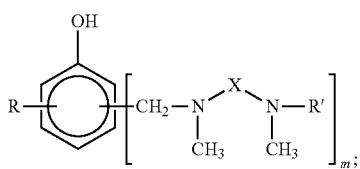

(I-A)

wherein:

m is 1, 2, or 3;

R is a hydrogen atom or a $C_1$-$C_{18}$ linear or branched alkyl or alkenyl group;

each R' independently is a hydrogen atom or a moiety having the formula:

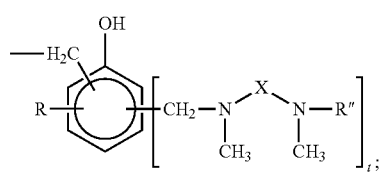

(I-B)

wherein:

R is defined as above;

t is 0, 1, or 2;

each R'' independently is a hydrogen atom or a moiety having the formula;

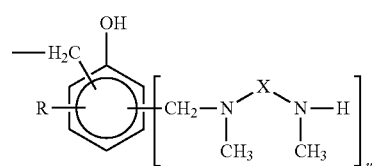

(I-C)

wherein:

R is defined as above;

u is 0, 1, or 2; and each X independently is a polyoxyalkylene moiety or a moiety having the formula:

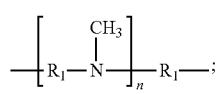

(II)

wherein:

$R_1$ is a $C_2$-$C_8$ linear or branched alkanediyl; and n is an integer in a range from 0 to 50, inclusive.

Amine curing agent compositions are provided in other aspects of the present invention. For example, an amine curing agent composition can be used to cure, harden, or crosslink an epoxy resin. An amine curing agent composition can comprise (i) any one of the three aforementioned Mannich base derivative compositions, provided immediately above; and (ii) at least one multifunctional amine having 3 or more active amine hydrogens.

In another aspect of the present invention, the amine curing agent composition can comprise from 1% to 99% of a Mannich base derivative composition. In another aspect, the Mannich base derivative composition can be used in amounts between about 10% and about 90% of the total amine curing agent composition. These percentages are weight percentages based upon the weight of the total amine curing agent composition. That is, the presence of additional components is not included in the weight percent calculation. For example, as used in the practice of manufacturing coatings, the amine curing agent composition can be provided in a diluent or solvent such as benzyl alcohol. Thus, when a percentage by weight of an amine component or a composition of the present invention is discussed, the quantity will exclude the effect of any diluents or other additives, unless stated otherwise. As an example, if 65 parts by weight of a Mannich base derivative composition of the present invention and 35 parts by weight of a multifunctional amine are used in conjunction with 40 parts by weight benzyl alcohol and an additive (e.g., a filler) in a given application, the weight percent of the Mannich base derivative composition is 65% based on the weight of the total amine curing agent composition. The presence of additional materials does not affect the determination of the percentage of the Mannich base derivative composition in relation to the total weight of the amine curing agent composition.

Another curing agent composition in accordance with the present invention comprises (i) about 90% to about 10% by weight, based on total amine curing agent composition, of a Mannich base derivative composition; and (ii) about 10% to about 90% by weight, based on total amine curing agent composition, of at least one multifunctional amine having 3 or more active amine hydrogens. In a further aspect, the at least one multifunctional amine having 3 or more active amine hydrogens also has 6 or more carbon atoms.

The present invention also contemplates an amine curing agent composition in which about 80% to about 20% by weight of the total amine curing agent composition is the Mannich base derivative composition. In yet another aspect, about 75% to about 25% by weight of the total amine curing agent composition is the Mannich base derivative composition. Again, in these contexts, the Mannich base derivative composition can be any of the three aforementioned Mannich base derivative compositions provided above.

The relative amount of the Mannich base derivative composition versus that of the multifunctional amine can vary depending upon, for example, the end-use article, its desired properties, and the fabrication method and conditions used to produce the end-use article. For instance, in amine-epoxy coating applications, incorporating more of the Mannich base derivative composition relative to the amount of the multifunctional amine generally results in coatings which have greater flexibility, a broader re-coat window, and that cure faster and/or can be cured at lower temperatures. Conversely, incorporating relatively more multifunctional amine generally results in coatings with improved chemical resistance and often higher ultimate hardness.

In accordance with another aspect of the present invention, an amine-epoxy composition is provided. For example, an amine-epoxy composition can comprise:

(a) a Mannich base derivative composition; and
(b) an epoxy component comprising at least one multifunctional epoxy resin.

Yet, in another aspect of the present invention, an amine-epoxy composition is provided, which comprises:

(a) an amine curing agent composition; and
(b) an epoxy component comprising at least one multifunctional epoxy resin.

In this aspect, the amine curing agent composition can comprise (i) any one of the three aforementioned Mannich base derivative compositions; and (ii) at least one multifunctional amine having 3 or more active amine hydrogens.

In a further aspect, the present invention contemplates a method for curing the amine-epoxy compositions indicated above. For example, the amine-epoxy composition can be cured at a temperature of less than or equal to about 23° C. In another aspect, the amine-epoxy composition is cured at a temperature of less than or equal to about 5° C. The amine-epoxy compositions of the present invention offer improved cure rates at temperatures at or below room temperature, including temperatures less than or equal to about 5° C., as compared to conventional amine-epoxy compositions.

The amine-epoxy compositions of the present invention comprise (a) a Mannich base derivative composition and, optionally, at least one multifunctional amine having 3 or more active amine hydrogens; and (b) an epoxy component comprising at least one multifunctional epoxy resin. Compositions obtained by curing the amine-epoxy compositions of the present invention, as well as articles of manufacture comprising these compositions, are also contemplated by the present invention. Such articles can include, but are not limiting to, a coating, an adhesive, a construction product, a flooring product, a composite product, and the like. For example, the article can be a coating which is applied to a metal or cementitious substrate. Additional components or additives can be used together with the compositions of the present invention to produce various articles of manufacture.

The present invention also provides methods of making an epoxy resin composition. One such method comprises:
(a) forming an amine component comprising a Mannich base derivative composition and optionally at least one multifunctional amine having 3 or more active amine hydrogens, and
(b) contacting the amine component with at least one multifunctional epoxy resin at a stoichiometric ratio of epoxy groups in the multifunctional epoxy resin to amine hydrogens in the amine component ranging from about 1.5:1 to about 1:1.5.

In accordance with the amine-epoxy compositions and methods of making an epoxy composition disclosed herein, the stoichiometric ratio of epoxy groups in the epoxy component to amine hydrogens in the amine component or composition ranges from about 1.5:1 to about 1:1.5. Yet, in another aspect, the stoichiometric ratio of epoxy groups in the epoxy component to amine hydrogens in the amine component or composition ranges from about 1.3:1 to about 1:1.3. These stoichiometric ratios are based on the total quantities of the respective amine and epoxy components. For example, if the amine component contains 65 parts by weight of a Mannich base derivative composition and 35 parts by weight of a multifunctional amine, the total amount of amine hydrogens from both the Mannich base derivative composition and the multifunctional amine are used to determine the stoichiometric ratio.

Additionally, it can be beneficial in the compositions of the present invention for all of the possible components to be liquids at room temperature. That is, the Mannich base derivative composition, the at least one multifunctional amine compound, and the at least one multifunctional epoxy resin compound can all be liquids at room temperature. In this disclosure, room temperature, or ambient temperature, is approximately 23° C.

Applicants disclose several types of ranges in the present invention. These include, but are not limited to, a range of weight percentages, a range of temperatures, a range of number of atoms, a range of molecular weights, a range of amine hydrogen equivalent weights, a range of amine values, a range of integers, and a range of stoichiometric ratios. When Applicants disclose or claim a range of any type, Applicants' intent is to disclose or claim individually each possible number that such a range could reasonably encompass, as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that "R" can be a $C_1$ to $C_{18}$ linear or branched alkyl or alkenyl group, or in alternative language having from 1 to 18 carbon atoms, as used herein, refers to a "R" group that can be selected independently from an alkyl or alkenyl group having 1, 2, 3, 4, 5, 6, 7, 8, 9, 10, 11, 12, 13, 14, 15, 16, 17, or 18 carbon atoms, as well as any range between these two numbers (for example, a $C_1$ to $C_{10}$ alkyl or alkenyl group), and also including any combination of ranges between these two numbers (for example, a $C_2$ to $C_6$ and $C_9$ to $C_{15}$ alkyl or alkenyl group).

Similarly, another representative example follows for the amine value of a Mannich base derivative composition in units of mg KOH/g. By a disclosure that the amine value is in a range from about 85 to about 910, Applicants intend to recite that the amine value can be selected from about 85, about 90, about 95, about 100, about 105, about 110, about 115, about 120, about 125, about 130, about 135, about 140, about 145, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 870, about 880, about 890, about 900, or about 910. Additionally, the amine value can be within any range from about 85 to about 910 (for example, the amine value is in a range from about 400 to about 900), and this includes any combination of ranges between about 85 and about 910 (for example, the amine value is in a range from about 100 to about 300, or from about 700 to about 880). Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions or formulations described herein. Combining additional materials or components can be done by any method known to one of skill in the art. Further, the term "contact product" includes mixtures, blends, solutions, slurries, reaction products, and the like, or combinations thereof. Although "contact product" can encompass reaction products of two or more components, it is not required for the respective components to react with one another.

While compositions and methods are described in terms of "comprising" various components or steps, the compositions and methods can also "consist essentially of" or "consist of" the various components or steps.

Mannich Base Derivative Compositions

Generally, the Mannich base derivative compositions of the present invention are polymeric, non-gelled compositions comprising amine compounds. One such composition comprises amine compounds illustrated by the following formula:

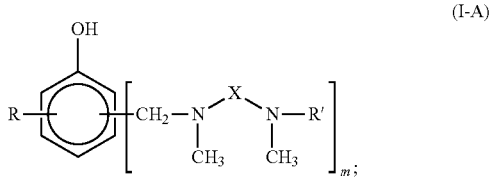

(I-A)

wherein:
m is 1, 2, or 3;
R is a hydrogen atom or a $C_1$-$C_{18}$ linear or branched alkyl or alkenyl group;
each R' independently is a hydrogen atom or a moiety having the formula:

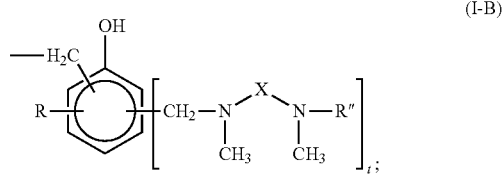

(I-B)

wherein:
R is defined as above;
t is 0, 1, or 2;
each R" independently is a hydrogen atom or a moiety having the formula;

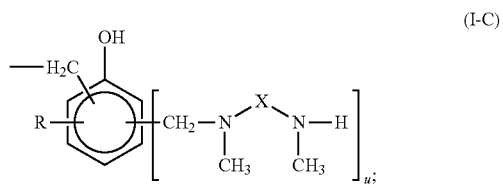

(I-C)

wherein:
R is defined as above;
u is 0, 1, or 2; and
each X independently is a polyoxyalkylene moiety or a moiety having the formula:

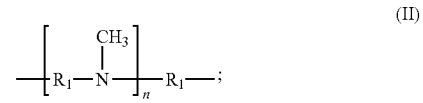

(II)

wherein:
$R_1$ is a $C_2$-$C_8$ linear or branched alkanediyl; and
n is an integer in a range from 0 to 50, inclusive.

Polymeric Mannich base derivative compositions encompassed by formula (I-A) having an amine hydrogen equivalent weight (AHEW) from about 98 to about 2100 are within the scope of the present invention. In another aspect, the composition has an AHEW in the range from about 100 to about 1700, or from about 105 to about 1350. In yet another aspect, the AHEW is in a range from about 105 to about 1000, from about 105 to about 750, or from about 105 to about 500. For example, the AHEW of the Mannich base derivative composition can be in a range from about 115 to about 300.

The amine value of the Mannich base derivative composition encompassed by formula (I-A) typically falls within a range from about 85 to about 910 mg KOH/g. The amine value of this composition can be within a range from about 100 to about 910, from about 130 to about 900, or from about 200 to about 890, in other aspects of this invention. For example, the amine value can be in a range from about 300 to about 890. In another aspect, the amine value is in a range from about 400 to about 900, from about 500 to about 900, or from about 600 to about 900. In a different aspect, the amine value of the Mannich base derivative composition is in a range from about 700 to about 880.

Formula (I-A) above, as well as formulas (I-B), (I-C), and (II), are not designed to show stereochemistry or isomeric positioning of the different moieties (e.g., these formulas are not intended to show cis or trans isomers), although such compounds are contemplated and encompassed by these formulas.

The integer m in formula (I-A) is 1, 2, or 3, while R can be a hydrogen atom or a $C_1$-$C_{18}$ linear or branched alkyl or alkenyl group. Unless otherwise specified, alkyl and alkenyl groups described herein are intended to include all structural isomers, linear or branched, of a given moiety; for example, all enantiomers and all diastereomers are included within this definition. As an example, unless otherwise specified, the term propyl is meant to include n-propyl and iso-propyl, while the term butyl is meant to include n-butyl, iso-butyl, t-butyl, sec-butyl, and so forth. For instance, non-limiting examples of octyl isomers include 2-ethyl hexyl and neooctyl. Suitable examples of alkyl groups which can be employed in the present invention include, but are not limited to, methyl, ethyl, propyl, butyl, pentyl, hexyl, heptyl, octyl, nonyl, decyl, docedyl, and the like. Other alkyl groups such as, for example, a $C_{14}$ alkyl, a $C_{15}$ alkyl, a $C_{16}$ alkyl, a $C_{18}$ alkyl, and the like, can also be used in this invention. In formula (I-A), R can be an alkenyl group, examples of which include, but are not limited to, ethenyl, propenyl, butenyl, pentenyl, hexenyl, heptenyl, octenyl, nonenyl, decenyl, and the like, as well as $C_{14}$ alkenyl, $C_{15}$ alkenyl, $C_{16}$ alkenyl, or $C_{18}$ alkenyl groups.

In one aspect of the present invention, R is a hydrogen atom. In another aspect, R is a methyl, ethyl, propyl, butyl, pentyl, hexyl, heptyl, octyl, nonyl, decyl, or docedyl group. Yet, in another aspect, R is an ethenyl, propenyl, butenyl, pentenyl, hexenyl, heptenyl, octenyl, nonenyl, or decenyl group. Additionally, R can be a hydrogen atom, a methyl group, an ethyl group, a propyl group, a butyl group, a tert-butyl group, an octyl group, a nonyl group, a dodecyl group, a $C_{15}$ alkyl group, or a $C_{15}$ alkenyl group, in other aspects of the present invention.

Each R' in formula (I-A) independently is a hydrogen atom or a moiety having the formula (I-B) presented above. In one aspect of this invention, for instance, each R' in formula (I-A) is a hydrogen atom. In formula (I-B), R is a hydrogen atom or a $C_1$-$C_{18}$ linear or branched alkyl or alkenyl group, as discussed above. The integer t in formula (I-B) is 0, 1, or 2, and each R" in formula (I-B) independently is a hydrogen atom or a moiety having the formula (I-C) presented above. In formula (I-C), R is as defined above, a hydrogen atom or a $C_1$-$C_{18}$ linear or branched alkyl or alkenyl group. The integer u in formula (I-C) is 0, 1, or 2.

Each X in formulas (I-A), (I-B), and (I-C) independently is a polyoxyalkylene moiety or a moiety having the formula:

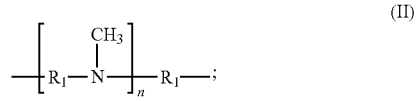

(II)

wherein:

$R_1$ is a $C_2$-$C_8$ linear or branched alkanediyl; and n is an integer in a range from 0 to 50, inclusive.

Generally, the polyoxyalkylene moiety comprises propyl ether repeating units, ethyl ether repeating units, or a combination thereof. For instance, the polyoxyalkylene moiety can be:

(III)

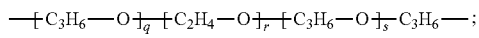

(IV)

wherein p, q, r, and s, independently, are integers in a range from 0 to 50, inclusive. Formulas (III) and (IV) above are not designed to show stereochemistry or isomeric positioning of the different moieties (e.g., these formulas are not intended to show cis or trans isomers), although such compounds are contemplated and encompassed by these formulas.

By describing $R_1$ in formula (II) as an "alkanediyl" moiety, Applicants are specifying the number of carbon atoms in the $R_1$ moiety, along with the number of hydrogen atoms required to conform to the rules of chemical valence for that diyl moiety. For example, as illustrated in the above formulas, the fact that $R_1$ is bonded to two other groups is consistent with this description of an alkanediyl moiety.

Unless otherwise specified, alkanediyl groups described herein are intended to include all structural isomers, linear or branched, of a given moiety; for example, all enantiomers and all diastereomers are included within this definition. As an example, unless otherwise specified, the term propanediyl is meant to include 1,1-propanediyl, 1,2-propanediyl, 1,3-propanediyl, and 2,2-propanediyl. Similarly, butanediyl is meant to include all stereo and regio diyl isomers of butane, for example, n-butane-1,1-diyl, n-butane-1,2-diyl, n-butane-1,3-diyl, n-butane-1,4-diyl, n-butane-2,3-diyl, 2-methylpropane-1,1-diyl, 2-methylpropane-1,3-diyl, and so forth.

It is within the scope of the present invention that $R_1$ in formula (II) is a $C_2$-$C_8$ linear or branched alkanediyl. In another aspect, $R_1$ is a $C_3$-$C_8$ linear or branched alkanediyl. In yet another aspect, $R_1$ is a $C_3$-$C_6$ linear or branched alkanediyl. For example, $R_1$ can be a $C_3$ or a $C_6$ linear alkanediyl.

The Mannich based derivative compositions of the present invention can be described as polymers, indicating that the compounds within the compositions can comprise at least one repeating unit. Applicants' use of the term "polymer" is meant to include all molecular weight polymers, including lower molecular weight polymers or oligomers. Since there is not an industry accepted cutoff in molecular weight between a polymer and an oligomer, Applicants have elected to use the term polymer throughout this disclosure and intend for the term polymer to encompass oligomers as well.

Since compounds of the present invention are polymeric, the compositions necessarily include mixtures of different size molecules, with different numbers of repeating units. Further, for a polymeric Mannich base composition comprising amine compounds having the formulas disclosed above, the integers n, p, q, r, and s, respectively and independently, can be zero.

For instance, the moiety within the brackets of formula (II) illustrates a repeating unit in a given molecule or compound, where the integer "n" represents the number of repeating units in that molecule or compound. Since the Mannich base derivative composition of the present invention represented by formula (I-A) is polymeric, it is represented by a mixture of molecules or compounds of various sizes, i.e., various values of n. It is within the scope of the present invention for the integer n to vary from 0 to 50 or more. In a different aspect, n in formula (II) ranges from 0 to 40, or from 0 to 30, or from 0 to 20, inclusive. In a further aspect, n ranges from 0 to 10, inclusive.

In a different aspect of the present invention, the integer n in formula (II) ranges from 1 to 50, for example, from 1 to 40, or from 1 to 30, inclusive. The integer n can range from 1 to 20, inclusive, in another aspect of the present invention. Further, n is an integer in a range from 1 to 10, inclusive, in still another aspect of the present invention. Yet, in another aspect, n is an integer in a range from 1 to 6, inclusive. It is understood that n represents an integer designating the number of repeating units for a single molecule or compound within the polymeric composition, where the polymeric composition has a distribution of values of n, a distribution of molecular sizes, and a distribution of molecular weights.

Similarly, the moiety having the formula (III) comprises a propyl ether repeating unit. One of skill in the art would recognize that such polymeric repeating units can be derived in a manner similar to propylene oxide polymerization. In formula (III), the integer "p" represents the number of repeating units in a molecule or compound within the polymeric composition. It is within the scope of the present invention for the integer p to vary from 0 to 50 or more. Alternatively, p in formula (III) ranges from 0 to 40, from 0 to 30, or from 0 to 20, inclusive. In a different aspect, p ranges from 0 to 10, inclusive. In accordance with another aspect of the present invention, however, p is in a range from 1 to 50, for example, from 1 to 30, from 1 to 20, or from 1 to 10, inclusive. The integer p can fall within a range from 1 to 6, inclusive, in yet another aspect of this invention.

The moiety having the formula (IV) comprises propyl ether and ethyl ether repeating units. One of ordinary skill in the art would recognize that such polymeric repeating units can be derived in a manner similar to ethylene oxide and propylene oxide polymerization, where a polyethylene oxide chain has been capped with polypropylene oxide repeating units. In formula (IV), the integers "q", "r", and "s" represent the number of repeating units in a molecule or compound within the polymeric composition. It is within the scope of the present invention for each of these integers, independently, to range from 0 to 50 or more. In some cases, these integers, independently, fall within a range from 0 to 30, or from 0 to 20, inclusive. For example, the integers q, r, and s can vary independently from 0 to 10, or from 0 to 6, inclusive. Alternatively, the integers q, r, and s can vary independently from 1 to 40, from 1 to 30, or from 1 to 20, in another aspect of the present invention. Yet, in another aspect, the integers q, r, and s range independently from 1 to 10, or from 1 to 6, inclusive.

In accordance with the present invention, methods of making these novel polymeric Mannich base derivative compositions are disclosed. One of the reactants used to produce these novel compositions is an N,N'-dimethyl secondary diamine polymer, or methylamine-terminated polymer, such as, for example, methylamine-terminated poly-(N-methylazetidine) or methylamine-terminated polyoxypropylene. These polymeric materials, and methods for synthesizing these materials, are disclosed in U.S. patent application Ser. No. 11/584,388, filed on Oct. 20, 2006, which is incorporated herein by reference in its entirety.

The $M_n$ data of these N,N'-dimethyl secondary diamine polymers, and the data presented in Examples 1-5 that follow, were determined using a Gas Chromatography (GC) technique. This procedure used a Hewlett-Packard 6890 Gas Chromatograph equipped with a flame ionization detector. The inlet was operated at 275° C. with a 10:1 split ratio. The GC technique used an initial temperature of 50° C. with an initial hold time of 2 minutes, followed by increasing the temperature at a rate of 7° C. per minute, up to a maximum temperature of 285° C. The maximum temperature was held for an additional 30 minutes. The column was a nominal 30 meter HP-5 (5% phenyl methyl silicone, 95% dimethyl silicone) capillary column with a nominal diameter of 530 μm and a nominal film thickness of 2.65 μm. The initial flow rate of helium was 4.2 mL/min.

The $M_n$ was determined by assuming that the mass of eluting material was proportional to the area percent obtained by this GC technique. Reaction by-products were not included in the $M_n$ calculation, and only polymeric species with sufficient volatility to elute under the GC conditions given above were included in the calculation. The $M_n$ was determined by dividing each area percent (proportional to mass) by the molecular weight of that particular polymeric species to yield the relative moles of that species. The sum of the relative moles of the polymeric species was then divided into the total area percent of the polymeric species to give $M_n$. The total area percent excludes the area percent of reaction by-products. As will be recognized by those skilled in the art, as $M_n$ increases, at some point an alternative technique such as Gel Permeation Chromatography (GPC) can be employed for the measurement of $M_n$, due to the low volatility of the higher molecular weight species in the distribution. For some N,N'-dimethyl secondary diamine polymers, this occurs when $M_n$ exceeds about 400.

Illustrative examples of N,N'-dimethyl secondary diamine polymers which can be used to produce Mannich base derivative compositions in accordance with the present invention include, but are not limited to, methylamine-terminated poly-(N-methylazetidine), methylamine-terminated polyoxypropylene, methylamine-terminated polyoxypropylene polyoxyethylene copolymers, methylamine-terminated poly-(N-methylazacycloheptane), and the like, or any combination thereof. A non-limiting example of the synthesis of methylamine-terminated poly-(N-methylazacycloheptane) is illustrated in Example 1, while non-limiting examples of the synthesis of methylamine-terminated poly-(N-methylazetidine) are demonstrated in Examples 2-5. A constructive example of the synthesis of methylamine-terminated polyoxypropylene is shown in Constructive Example 6 that follows. Additional information on these materials can be found in U.S. patent application Ser. No. 11/584,388, filed on Oct. 20, 2006, the disclosure of which is incorporated herein by reference in its entirety.

One method of making a polymeric Mannich base derivative composition of the present invention comprises contacting at least one aldehyde compound, at least one phenol compound, and at least one N,N'-dimethyl secondary diamine polymer having a number-average molecular weight ($M_n$) from about 140 to about 1000. The compounds produced also can be referred to as Mannich base derivatives of an N,N'-dimethyl secondary diamine polymer. Generally, in this method of synthesis, the molar ratio of the at least one aldehyde compound to the at least one phenol compound is less than or equal to about 3:1, and the molar ratio of the at least one N,N'-dimethyl secondary diamine polymer to the at least one aldehyde compound is greater than or equal to about 1:1. Non-limiting examples of the synthesis of Mannich base derivative compositions in accordance with this method of the present invention are illustrated in Examples 18-25.

Mannich bases are the condensation products of phenol or substituted phenols, multifunctional amines, and an aldehyde, for example, formaldehyde. A commonly employed phenol stream used for the preparation of Mannich bases is cardanol, which comprises phenol substituted with $C_{15}$ unsaturated fatty chains in the meta position. These latter Mannich bases are often referred to in the industry as phenalkamines. One method for the preparation of Mannich bases is the direct reaction of at least one phenol or substituted phenol, at least one multifunctional amine, and least one aldehyde, such as formaldehyde. This method of synthesizing a Mannich base is illustrated in the general reaction scheme presented below, where the multifunctional amine is a di-primary amine:

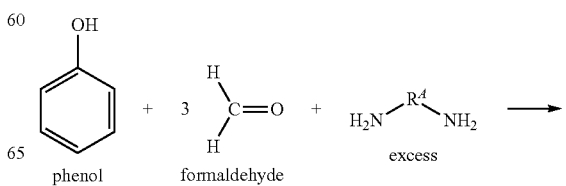

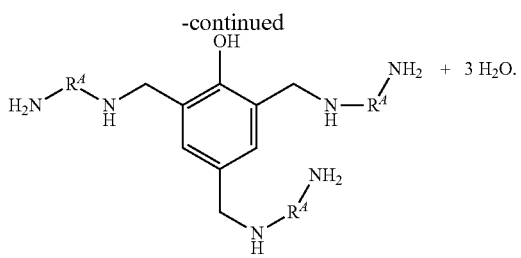

+ 3 H₂O

The preparation of Mannich bases from phenols, aldehydes and primary or secondary amines or ammonia is well known to those of skill in the art. For example, J. March, Advanced Organic Chemistry, Third Ed., John Wiley and Sons, New York, 1985, pages 496 and 800-802, which are incorporated herein by reference, provides general Mannich base reaction schemes.

Conventional Mannich base compounds known in the art (i.e., not the polymeric Mannich base derivative compositions of the present invention) have been employed in amine-epoxy formulations because, generally, they cure quickly at low temperatures. However, amine-epoxy coatings using these conventional Mannich base compounds often manifest blush, carbamate and exudate, and have poor flexibility. Further, Mannich bases produced by this direct reaction generally contain large amounts of residual phenol. Phenol is a toxic chemical, and its presence at levels greater than 1% in a chemical mixture or composition generally requires special disposal techniques, special labeling, and the use of personal protective equipment to minimize worker exposure, all of which detract from the commercial acceptance of these products.

Attempts to adjust the stoichiometric ratio to drive the reaction to complete conversion of phenol generally causes the reaction to gel before the phenol content is reduced to less than about 1%. One way to avoid gelation is to adjust the stoichiometric ratio of reactants such that large quantities of residual phenol necessarily remain in the final product. Thus, a typical recipe for a traditional Mannich base curing agent comprises approximately 1 mole of formaldehyde to about 2 to 3 moles of phenol to about 3 moles of multifunctional amine. Generally, Mannich base derivative compositions of the present invention are non-gelled compositions.

In accordance with one aspect of the present invention, a Mannich base derivative composition is provided. This composition comprises a Mannich base reaction product of:

(a) at least one aldehyde compound;
(b) at least one phenol compound; and
(c) at least one N,N'-dimethyl secondary diamine polymer having a $M_n$ from about 140 to about 1000.

The at least one phenol compound employed in the preparation of the Mannich base derivatives by this direct reaction process is phenol or a mono-substituted $C_1$ to $C_{18}$ alkyl phenol or alkenyl phenol. All isomers (ortho, meta and para) of the mono-substituted phenol may be employed. Non-limiting examples of suitable phenol compounds include phenol, cresol, butylphenol, t-butylphenol, octylphenol, nonylphenol, dodecylphenol, cardanol, and the like, or combinations thereof. Cardanol is derived from cashew nut shell liquid and contains a phenol substituted with $C_{15}$ saturated and unsaturated fatty chains in the meta position.

For the at least one aldehyde compound, formaldehyde can be used in any of the commercially available forms (e.g., a liquid form) employed for conventional condensation reactions, which are well known to those skilled in the art. The liquid form of formaldehyde may include polymeric formaldehyde species also known as paraformaldehyde. Formalin is another form of formaldehyde that may be employed. Other $C_2$ to $C_{12}$ aldehydes can also be employed in the direct Mannich base reaction.

Typically, the molar ratio of the at least one aldehyde compound (e.g., formaldehyde) to the at least one phenol compound (e.g., unsubstituted phenol) employed in the preparation of the Mannich base derivative of an N,N'-dimethyl secondary diamine polymer will be less than or equal to about 3:1. If the ratio is much greater than about 3:1, it is generally believed that the excess formaldehyde (or other aldehyde compound) will couple amines with a methylene unit, which could subsequently be hydrolyzed by atmospheric water when the composition is employed to cure epoxy resins, resulting in the release of formaldehyde. With a mono-substituted alkyl phenol or alkenyl phenol, the molar ratio of the at least one aldehyde compound to the at least one phenol compound is generally less than about 2:1.

The lower limit on the molar ratio of the at least one aldehyde compound to the at least one phenol compound for some applications is about 1:1. As this ratio decreases, it becomes increasingly more difficult to decrease the concentration of residual free phenols. Furthermore, the concentration of phenolic OH groups in the overall composition is reduced, which tends to decrease the rate of reaction of the Mannich base compounds with epoxy resins, often resulting in longer curing times for amine-epoxy compositions.

In accordance with one aspect of the invention employing unsubstituted phenol, the molar ratio of formaldehyde or other aldehyde compound to phenol is within a range from about 2:1 to about 3:1. For example, the molar ratio can be in a range from about 2.2:1 to about 3:1, or from about 2.5:1 to about 2.9:1. In an aspect of the invention employing a mono-substituted phenol, at the meta position, the molar ratio of formaldehyde or other aldehyde to the at least one phenol compound is from about 1:1 to about 3:1, such as, for example, from about 1.3:1 to about 2.5:1, or from about 1.5:1 to about 1.9:1. In an aspect employing a mono-substituted phenol, at the ortho or para position, the molar ratio of formaldehyde or other aldehyde to the at least one phenol compound is from about 1:1 to about 2.5:1. Further, the molar ratio can be from about 1:1 to about 2:1, or from about 1.5:1 to about 1.9:1.

The molar ratio of the at least one N,N'-dimethyl secondary diamine polymer to the at least one aldehyde compound (e.g., formaldehyde) is generally greater than or equal to about 1:1 to minimize the viscosity of the final product, and to prevent gelation in cases where unsubstituted phenol is employed as the at least one phenol compound. However, if a higher viscosity product is desired, lower molar ratios can be employed, so long as the reaction product does not gel. In accordance with one aspect of the present invention, the molar ratio of at least one N,N'-dimethyl secondary diamine polymer to the at least one aldehyde compound (e.g., formaldehyde) ranges from about 1:1 to about 3:1, for example, about 1:1 to about 2.5:1. Molar ratios above about 2.5:1 can be employed, but the phenolic OH concentration will be reduced as dictated by the formaldehyde to phenol ratios described above. This will likely also increase the level of free amine, which tends to negatively impact the surface appearance of amine-epoxy coatings. In another aspect, the molar ratio of the at least one diamine polymer to the at least one aldehyde compound is in a range from about 1.2:1 to about 1.8:1.

Various modifications of the general procedure for the preparation of the Mannich base compounds by the direct process described above can be used, and are within the scope of this invention. For example, phenol (or substituted phenol)

and formaldehyde (or other aldehyde compound) can be mixed together and heated to about 100° C., followed by the addition of the N,N'-dimethyl secondary diamine polymer. Additional heating and removal of water via distillation yields the Mannich base derivative. Alternatively, a pre-mixed solution of phenol (or substituted phenol) and formaldehyde (or other aldehyde compound) can be added to the N,N'-dimethyl secondary diamine polymer, followed by distillation to remove water. In another procedure, formaldehyde (or other aldehyde compound) can be added to the N,N'-dimethyl secondary diamine polymer, followed by the addition of the phenol compound, heating, and then distilling to remove water. Also, the N,N'-dimethyl secondary diamine polymer and the phenol compound can be mixed together, followed by the addition of formaldehyde (or other aldehyde compound) and the removal of water.

In one aspect of the present invention, the phenol or substituted phenol is contacted with the N,N'-dimethyl secondary diamine polymer. Liquid formaldehyde is then added to the reaction mixture at room temperature or slightly elevated temperature, so that the exotherm is controlled. The reaction mixture is subsequently heated to complete the reaction. The reaction temperature is generally in the range from about 50 to about 100° C., although higher or lower temperatures than these can be employed. In another aspect, the reaction temperature ranges from about 70 to about 90° C. After reaching reaction completion, the temperature is then increased to remove water, and methanol if formalin was employed as the formaldehyde source.

Generally, the at least one aldehyde compound, the at least one phenol compound, and the at least one N,N'-dimethyl secondary diamine polymer can be contacted in any order or sequence, and subsequently reacted to form the resultant Mannich base derivative composition.

A Mannich base derivative composition, therefore, can comprise a Mannich base reaction product of at least one aldehyde compound, at least one phenol compound, and at least one N,N'-dimethyl secondary diamine polymer having a $M_n$ from about 140 to about 1000. Generally, the molar ratio of the at least one aldehyde compound to the at least one phenol compound is less than or equal to about 3:1, and the molar ratio of the at least one N,N'-dimethyl secondary diamine polymer to the at least one aldehyde compound is greater than or equal to about 1:1. In these and other aspects, the at least one aldehyde compound can comprise formaldehyde. In another aspect, the at least one phenol compound comprises phenol, cresol, t-butyl phenol, nonyl phenol, cardanol, or a combination thereof. In yet another aspect, the at least one N,N'-dimethyl secondary diamine polymer comprises methylamine-terminated poly-(N-methyl-azetidine), methylamine-terminated poly-(N-methyl-azacycloheptane), or a combination thereof.

The Mannich base derivative composition comprising a reaction product of at least one aldehyde compound, at least one phenol compound, and at least one N,N'-dimethyl secondary diamine polymer generally has an AHEW from about 98 to about 1350. In another aspect, this composition has an AHEW in the range from about 100 to about 1200, or from about 105 to about 1000. In yet another aspect, the AHEW is in a range from about 105 to about 800, from about 105 to about 600, or from about 105 to about 400. For example, the AHEW of the Mannich base derivative composition, in this aspect, can be in a range from about 115 to about 300.

Similarly, the amine value of this Mannich base derivative composition typically falls within a range from about 85 to about 910 mg KOH/g. The amine value of this composition can be within a range from about 100 to about 910, from about 130 to about 900, or from about 200 to about 890, in other aspects of this invention. For example, the amine value can be in a range from about 300 to about 890. In another aspect, the amine value is in a range from about 400 to about 900, from about 500 to about 900, or from about 600 to about 900. In a different aspect, the amine value of the Mannich base derivative composition is in a range from about 700 to about 880.

In accordance with another aspect of the present invention, a Mannich base derivative composition is provided which comprises a reaction product of:
(a) at least one di-substituted or tri-substituted Mannich base compound; and
(b) at least one N,N'-dimethyl secondary diamine polymer having a $M_n$ from about 140 to about 1000.

This composition employs an exchange reaction, which can produce substantially phenol-free Mannich base derivatives of at least one N,N'-dimethyl secondary diamine polymer. Generally, the molar ratio of the at least one N,N'-dimethyl secondary diamine polymer to the at least one di-substituted or tri-substituted Mannich base compound is in a range from about 1:1 to about 6:1. Non-limiting examples of the synthesis of Mannich base derivative compositions in accordance with this method of the present invention are illustrated in Examples 7-10 and 26.

In one aspect, the at least one di-substituted or tri-substituted Mannich base compound comprises bis-(dimethylaminomethyl)phenol, tris-(dimethylaminomethyl)phenol, or a combination thereof. The at least one N,N'-dimethyl secondary diamine polymer can comprise methylamine-terminated poly-(N-methyl-azetidine), methylamine-terminated poly-(N-methyl-azacycloheptane), or a combination thereof, in another aspect of this invention. Yet, in another aspect, the at least one N,N'-dimethyl secondary diamine polymer can comprise a polyoxyalkylene diamine, such as methylamine-terminated polyoxypropylene or a methylamine-terminated polyoxypropylene polyoxyethylene copolymer. In an exchange reaction involving tris-(dimethylaminomethyl)phenol, for example, dimethylamine is substituted by the diamine polymer to yield the Mannich base derivatives of the present invention. The tri-substituted Mannich base compound, tris-(dimethylaminomethyl)phenol, is commercially available from Air Products and Chemicals, Inc., as Ancamine® K54.

The Mannich base compounds utilized in the exchange process can be derived from the same phenols referred to above in describing the direct reaction process, such as, phenol, t-butylphenol, and cardanol. The secondary amine used for exchange can be any secondary amine of sufficient volatility to be easily removed from the reaction mixture by distillation. As it pertains to the present invention, therefore, it is beneficial if the boiling point of the secondary amine is sufficiently different from the boiling point of the diamine polymer used. Suitable secondary amines include, but are not limited to, dimethylamine, diethylamine, dipropylamine, dibutylamine, piperidine, pyrrolidine, morpholine, methylpiperazine, and the like, or combinations thereof.

Typically, the lower limit of the molar ratio of the at least one N,N'-dimethyl secondary diamine polymer to the at least one tri-substituted Mannich base compound (e.g., tris-(dimethylaminomethyl)phenol) is the molar ratio which still yields a non-gelled reaction product. Often, the molar ratio of the at least one diamine polymer to the at least one tri-substituted Mannich base compound is in a range from about 2:1 to about 6:1, for example, about 3:1 to about 4.5:1. When conducting the exchange reaction with a di-substituted Mannich base compound, the molar ratio of the at least one diamine polymer to the at least one di-substituted Mannich base compound employed can be in a range from about 1:1 to about 4.5:1. In another aspect, the molar ratio is in range from about 2:1 to about 3:1. As the molar ratio is decreased, the viscosity of the reaction product generally increases. Conversely, as the molar ratio is increased, generally the level of free diamine polymer will increase, as will the cure time with an epoxy resin.

An amine exchange reaction of the present invention can be conducted by heating and contacting the at least one di-substituted or tri-substituted Mannich base compound with the at least one N,N'-dimethyl secondary diamine polymer, generally while agitating, to temperatures of at least about 100° C. In other aspects, the reaction temperature can be within a range from about 130° C. to about 220° C., or from about 140° C. to about 180° C. Optionally, the reactants can be contacted in the presence of an inert solvent or diluent. The secondary amine which is liberated in the reaction can be distilled into a cooled receiver.

The Mannich base derivative composition comprising a reaction product of at least one di-substituted or tri-substituted Mannich base compound and at least one N,N'-dimethyl secondary diamine polymer generally has an AHEW from about 107 to about 2100. In another aspect, this composition has an AHEW in the range from about 110 to about 1500, or from about 110 to about 1000. In yet another aspect, the AHEW is in a range from about 110 to about 800, from about 110 to about 600, or from about 115 to about 400. For example, the AHEW of the Mannich base derivative composition, in this aspect, can be in a range from about 115 to about 300.

Similarly, the amine value of this Mannich base derivative composition typically falls within a range from about 130 to about 900 mg KOH/g. The amine value of this composition can be within a range from about 150 to about 910, from about 200 to about 900, or from about 250 to about 890, in other aspects of this invention. For example, the amine value can be in a range from about 300 to about 890. In another aspect, the amine value is in a range from about 400 to about 900, from about 500 to about 900, or from about 600 to about 900. In a different aspect, the amine value of the Mannich base derivative composition is in a range from about 700 to about 880.

Multifunctional Amine

Compositions in accordance with the present invention can comprise at least one multifunctional amine. Multifunctional amine, as used herein, describes compounds with amine functionality and which contain three (3) or more active amine hydrogens.

It can be beneficial to limit the volatility of the specific multifunctional amine used in some applications where worker exposure and safety issues may arise. Thus, in one aspect of the present invention, the at least one multifunctional amine contains 6 or more carbon atoms. In another aspect, the at least one multifunctional amine contains 8 or more carbon atoms. In yet another aspect, the at least one multifunctional amine contains 12 or more carbon atoms.

Non-limiting examples of multifunctional amines that are within the scope of the present invention include, but are not limited to, an aliphatic amine; a cycloaliphatic amine; an aromatic amine; a Mannich base derivative of an aliphatic amine, a cycloaliphatic amine, or an aromatic amine; a polyamide derivative of an aliphatic amine, a cycloaliphatic amine, or an aromatic amine; an amidoamine derivative of an aliphatic amine, a cycloaliphatic amine, or an aromatic amine; an amine adduct derivative of an aliphatic amine, a cycloaliphatic amine, or an aromatic amine; and the like; or any combination thereof. The Mannich base derivatives disclosed in this section are not the Mannich base derivatives of N,N'-dimethyl secondary diamine polymers of the present invention.

More than one multifunctional amine can be used in the compositions of the present invention. For example, the at least one multifunctional amine can comprise an aliphatic amine and a Mannich base derivative of a cycloaliphatic amine. Also, the at least one multifunctional amine can comprise one aliphatic amine and one different aliphatic amine.

Exemplary aliphatic amines include polyethylene amines (triethylenetetramine, tetraethylenepentamine, pentaethylenehexamine and the like), 1,6-hexanediamine, 3,3,5-trimethyl-1,6-hexanediamine, 3,5,5-trimethyl-1,6-hexanediamine, 2-methyl-1,5-pentanediamine (commercially available as Dytek-A), bis-(3-aminopropyl)amine, N,N'-bis-(3-aminopropyl)-1,2-ethanediamine, aminoethylpiperazine, and the like, or combinations thereof. Additionally, the poly(alkylene oxide) diamines and triamines commercially available under the Jeffamine name from Huntsman Corporation, are useful in the present invention. Illustrative examples include, but are not limited to, Jeffamine® D-230, Jeffamine® D-400, Jeffamine® D-2000, Jeffamine® D-4000, Jeffamine® T-403, Jeffamine® EDR-148, Jeffamine® EDR-192, Jeffamine® C-346, Jeffamine® ED-600, Jeffamine® ED-900, Jeffamine® ED-2001, and the like, or combinations thereof.

Cycloaliphatic and aromatic amines include, but are not limited to, 1,2-diaminocyclohexane, 1,3-diaminocyclohexane, 1,4-diaminocyclohexane, hydrogenated ortho-toluenediamine, hydrogenated meta-toluenediamine, metaxylylene diamine, hydrogenated metaxylylene diamine (referred to commercially as 1,3-BAC), isophorone diamine, various isomers of norbornane diamine, 3,3'-dimethyl-4,4'-diaminodicyclohexyl methane, 4,4'-diaminodicyclohexyl methane, 2,4'-diaminodicyclohexyl methane, a mixture of methylene bridged poly(cyclohexyl-aromatic)amines, and the like, or combinations thereof. The mixture of methylene bridged poly(cyclohexyl-aromatic)amines is abbreviated as either MBP-CAA or MPCA, and is described in U.S. Pat. No. 5,280,091, which is incorporated herein by reference in its entirety. In one aspect of the present invention, the at least one multifunctional amine is a mixture of methylene bridged poly(cyclohexyl-aromatic)amines (MPCA).

Mannich base derivatives suitable for use as a multifunctional amine can be made by the reaction of the above described aliphatic amines, cycloaliphatic amines, or aromatic amines with phenol or a substituted phenol and formaldehyde. An exemplary substituted phenol used to make Mannich bases with utility in the present invention is cardanol, which is obtained from cashew nut shell liquid. Alternatively, Mannich bases can be prepared by an exchange reaction of a multifunctional amine with a tertiary amine containing a Mannich base, such as tris-(dimethylaminomethyl)phenol (commercially available as Ancamine® K54 from Air Products and Chemicals, Inc.) or bis-(dimethylaminomethyl)phenol. Polyamide derivatives can be prepared by the reaction of an aliphatic amine, cycloaliphatic amine, or aromatic amine with dimer fatty acid, or mixtures of a dimer fatty acid and a fatty acid. Amidoamine derivatives can be prepared by the reaction of an aliphatic amine, cycloaliphatic amine, or aromatic amine with fatty acids. Amine adducts can be prepared by the reaction of an aliphatic amine, cycloaliphatic amine, or aromatic amine with an epoxy resin, for example, with the diglycidyl ether of bisphenol-A, the diglycidyl ether of bisphenol-F, or epoxy novolac resins. The aliphatic, cycloaliphatic, and aromatic amines also can be adducted with monofunctional epoxy resins, such as phenyl glycidyl ether, cresyl glycidyl ether, butyl glycidyl ether, other alkyl glycidyl ethers, and the like.

Multifunctional Epoxy Resin

Amine-epoxy compositions of the present invention comprise an epoxy component, the epoxy component comprising at least one multifunctional epoxy resin. Multifunctional epoxy resin, as used herein, describes compounds containing 2 or more 1,2-epoxy groups per molecule. Epoxide compounds of this type are described in Y. Tanaka, "Synthesis and Characteristics of Epoxides", in C. A. May, ed., Epoxy Resins Chemistry and Technology (Marcel Dekker, 1988), which is incorporated herein by reference.

One class of epoxy resins suitable for use in the present invention comprise the glycidyl ethers of polyhydric phenols, including the glycidyl ethers of dihydric phenols. Illustrative examples include, but are not limited to, the glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl)propane, 2,2-bis-(4-hydroxyphenyl)-propane (commercially known as bisphenol A), bis-(4-hydroxyphenyl)-methane (commercially known as bisphenol F, and which may contain varying amounts of 2-hydroxyphenyl isomers), and the like, or any combination thereof. Additionally, advanced dihydric phenols of the following structure also are useful in the present invention:

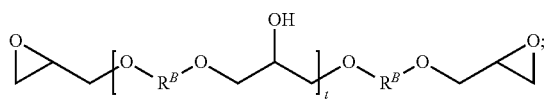

where t is an integer, and $R^B$ is a divalent hydrocarbon radical of a dihydric phenol, such as those dihydric phenols listed above. Materials according to this formula can be prepared by polymerizing mixtures of a dihydric phenol and epichlorohydrin, or by advancing a mixture of a diglycidyl ether of the dihydric phenol and the dihydric phenol. While in any given molecule the value of t is an integer, the materials are invariably mixtures which can be characterized by an average value of t which is not necessarily a whole number. Polymeric materials with an average value of t between 0 and about 7 can be used in one aspect of the present invention.

In another aspect, epoxy novolac resins, which are the glycidyl ethers of novolac resins, can be used as multifunctional epoxy resins in accordance with the present invention. In yet another aspect, the at least one multifunctional epoxy resin is a diglycidyl ether of bisphenol-A (DGEBA), an advanced or higher molecular weight version of DGEBA, a diglycidyl ether of bisphenol-F, an epoxy novolac resin, or any combination thereof. Higher molecular weight versions or derivatives of DGEBA are prepared by the advancement process, where excess DGEBA is reacted with bisphenol-A to yield epoxy terminated products. The epoxy equivalent weights (EEW) for such products ranges from about 450 to 3000 or more. Because these products are solid at room temperature, they are often referred to as solid epoxy resins.

DGEBA or advanced DGEBA resins are often used in coating formulations due to a combination of their low cost and generally high performance properties. Commercial grades of DGEBA having an EEW ranging from about 174 to about 250, and more commonly from about 185 to about 195, are readily available. At these low molecular weights, the epoxy resins are liquids and are often referred to as liquid epoxy resins. It is understood by those skilled in the art that most grades of liquid epoxy resin are slightly polymeric, since pure DGEBA has an EEW of 174. Resins with EEW's between 250 and 450, also generally prepared by the advancement process, are referred to as semi-solid epoxy resins because they are a mixture of solid and liquid at room temperature.

Depending upon the end-use application, it can be beneficial to reduce the viscosity of the compositions of the present invention by modifying the epoxy component. For example, the viscosity can be reduced to allow an increase in the level of pigment in a formulation or composition while still permitting easy application, or to allow the use of a higher molecular weight epoxy resin. Thus, it is within the scope of the present invention for the epoxy component, which comprises at least one multifunctional epoxy resin, to further comprise a monofunctional epoxide. Examples of monoepoxides include, but are not limited to, styrene oxide, cyclohexene oxide, ethylene oxide, propylene oxide, butylene oxide, and the glycidyl ethers of phenol, cresols, tert-butylphenol, other alkyl phenols, butanol, 2-ethylhexanol, $C_4$ to $C_{14}$ alcohols, and the like.

Miscellaneous Additives

Compositions of the present invention can be used to produce various articles of manufacture. Depending on the requirements during the manufacturing of or for the end-use application of the article, various additives can be employed in the formulations and compositions to tailor specific properties. These additives include, but are not limited to, solvents, accelerators, plasticizers, fillers, fibers such as glass or carbon fibers, pigments, pigment dispersing agents, rheology modifiers, thixotropes, flow or leveling aids, defoamers, or any combination thereof. It is understood that other mixtures or materials that are known in the art can be included in the compositions or formulations and are within the scope of the present invention.

Further, compositions within the scope of the present invention can be solventless, also referred to as solvent-free or 100% solids. Alternatively, these compositions can further comprise at least one solvent (a solvent is also referred to as a diluent). Often, a solvent or mixture of solvents is chosen to give a specific evaporation rate profile for the composition or formulation, while maintaining solubility of the components of the formulation.

Articles

The present invention also is directed to articles of manufacture comprising the compositions disclosed herein. For example, an article can comprise a cured amine-epoxy composition which comprises the contact product of an amine curing agent component and an epoxy component. The amine curing agent component can comprise at least one Mannich base derivative of an N,N'-dimethyl secondary diamine polymer and at least one multifunctional amine. The epoxy component can comprise at least one multifunctional epoxy resin. Optionally, various additives can be present in the compositions or formulations used to produce fabricated articles, dependent upon the desired properties. These additives can include, but are not limited to, solvents, accelerators, plasticizers, fillers, fibers such as glass or carbon fibers, pigments, pigment dispersing agents, rheology modifiers, thixotropes, flow or leveling aids, defoamers, or any combination thereof.

Articles in accordance with the present invention include, but are not limited to, a coating, an adhesive, a construction product, a flooring product, or a composite product. Coatings based on these amine-epoxy compositions can be solvent-free or can contain solvents or diluents as needed for the particular application. For example, coatings with solids content greater than 50%, greater than 65%, greater than 75%, or greater than 85%, are within the scope of the present invention. Coatings can contain various types and levels of pigments for use in paint applications.

Numerous substrates are suitable for the application of coatings of this invention with proper surface preparation, as is well known to one of ordinary skill in the art. Such substrates include, but are not limited to, concrete and various types of metals and alloys, such as steel and aluminum. For example, the low temperature cure, good surface appearance when applied at room temperature, and good flexibility properties of the coatings of the present invention make them suitable for the painting or coating of large metal objects or cementitious substrates which must be painted and/or cured at room temperature or colder conditions, including ships, bridges, industrial plants and equipment, and floors. Coatings of this invention can be applied and cured at temperatures ranging from about −10° C. to about 50° C., or alternatively, at temperatures ranging from about 0° C. to about 35° C. As needed, these coatings also can be force cured at higher temperatures, which often can improve the flexibility of the cured material.

Coatings of this invention can be applied by any number of techniques including spray, brush, roller, paint mitt, and the like. In order to apply very high solids content or 100% solids coatings of this invention, plural component spray application equipment can be used, in which the amine and epoxy components are mixed in the lines leading to the spray gun, in the spray gun itself, or by mixing the two components together as they leave the spray gun. Using this technique can alleviate limitations with regard to the pot life of the formulation, which typically decreases as both the amine reactivity and the solids content increases. Heated plural component equipment can be employed to reduce the viscosity of the components, thereby improving ease of application.

Construction and flooring applications include compositions comprising the amine-epoxy compositions of the present invention in combination with concrete or other materials commonly used in the construction industry. Compositions of the present invention can be used in the construction of epoxy-based floors, often in applications requiring better mechanical properties (e.g., improved tensile strength or improved compressive strength) or better elongation than that normally obtained from cementitious or other similar types of flooring materials. Crack injection and crack filling products also can be prepared from the compositions disclosed herein, as well as polymer modified cements, tile grouts, and the like. Non-limiting examples of composite products or articles comprising amine-epoxy compositions disclosed herein include tennis rackets, skis, bike frames, airplane wings, glass fiber reinforced composites, and other molded products.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Coatings of amine-epoxy compositions were prepared and tested as follows. Hardener mixtures or compositions, including amine compositions in accordance with the present invention, were prepared by contacting and mixing the components given in the tables that follow. The respective hardener mixture or composition, or the individual hardener, was then mixed with a multifunctional epoxy resin at the use level indicated in the tables in parts per hundred weight resin (PHR). The epoxy resin used in these examples was the diglycidyl ether of bisphenol-A (DGEBA), grade D.E.R.™ 331 with an EEW in the range of 182 to 192. This epoxy resin is commercially available from the Dow Chemical Company.

In Examples 11-17 and 27-41, clear coatings were applied to standard glass panels to produce samples for drying time testing using a Beck-Koller drying time recorder and for hardness development by the Persoz pendulum hardness method. Clear coatings for drying time by the thumb twist method and for specular gloss testing were applied to uncoated, matte paper charts (AG5350, Byk). Coatings were applied at about 75 μm WFT (wet film thickness) using a Bird bar applicator resulting in dry film thicknesses ranging from approximately 60 to 70 μm. Coatings of Examples 11-17 and 27-35 were cured either at 5° C. and 80% RH (relative humidity) or 25° C. and 60% RH using a Weiss climate chamber (type WEKK0057). Coatings of Examples 36-41 were cured at 5° C. and 60% RH using the Weiss climate chamber. Persoz Hardness was measured at the times indicated in the tables.

Clear coatings for impact resistance and mandrel bend testing were applied to respectively cold-rolled steel test panels, ground one side (approximate size 76 mm×152 mm×0.8 mm thick) and cold-rolled steel, smooth finish (approximate size 76 mm×152 mm×0.5 mm thick), using a nominal 75 WFT wire bar. Metal test panels were obtained from Q Panel Lab Products. Films were cured according to the following schedules: (A) 14 days room temperature, room temperature being approximately 23° C.; (B) 14 days room temperature followed by 2 hours at 80° C.; or (C) 60 days room temperature. Dry film thicknesses were from about 60 to 80 μm following cure schedules A and C, and from about 50 to 55 μm following schedule B.

The mix viscosities for Examples 11-17 were determined using a Rheolab MC20 apparatus (Physica) equipped with a Viscotherm VT10 water bath and MC20 temperature control unit. The equipment was set up with the TEK 150 cone-plate and connected to a computer. After the apparatus was equilibrated at 25° C., the gap between the cone (MK22) and plate was set to approximately 50 μm. Samples were equilibrated at 25° C. for 24 hours before testing. After mixing as indicated, excess product running out of the gap was removed and the rotational viscosity of the mixed product was recorded at a 200 reciprocal second shear rate after 30 seconds.

Coating properties were measured in accordance with the standard test methods listed in Table 1. Waterspot resistance is tested by placing drops of water on the surface of the coating for a specified time and observing the impact on the coating. This test is used in the industry to determine if the surface of the coating is damaged or aesthetically impacted by extended contact with water or moisture.

TABLE 1

| Analytical test methods. | | |
|---|---|---|
| Property | Response | Test Method |
| Drying Time: Beck-Koller Recorder | Thin film set times, phases 1, 2 & 3 (hr) | ASTM D5895 |
| Drying Time: Thumb Twist Method | Set-to-touch and dry-to-handle time (hr) | ASTM D1640 |
| Specular Gloss | Gloss at 20° and 60° | ISO 2813, ASTM D523 |
| Persoz Pendulum Hardness | Persoz hardness (s) | ISO 1522, ASTM D4366 |
| Impact Resistance - Tubular Impact Tester | Direct and reverse impact (kg · cm) | ISO 6272, ASTM D2794 |
| Mandrel Bend Test: Cylindrical Bend | Elongation (%) | ISO 1519, ASTM D1737 |
| Mandrel Bend Test: Conical Bend | Elongation (%) | ISO 6860, ASTM D522 |

Example 1

Synthesis of Methylamine-Terminated poly-(N-methylazacycloheptane)

135 g of adipodinitrile, 50 g of isopropanol, and 2.7 g of Pd/Al$_2$O$_3$ catalyst were placed in a 1-liter stainless-steel batch pressure reactor equipped with a stirrer and 1-liter hydrogen ballast tank. The Pd/Al$_2$O$_3$ catalyst is commercially available from the Johnson-Mathey Corporation. The reactor was sealed and subsequently purged with nitrogen and hydrogen to remove any air from the reactor. While stirring the reactor contents, 85 g of anhydrous methylamine were added to the reactor. The reactor was then pressurized with hydrogen to 1.72 MPa (250 psi), and heated to 120° C. These conditions were maintained until the rate of hydrogen uptake from the ballast tank fell below 0.0034 MPa/min (0.5 psi/min). When this occurred, the reactor pressure was raised to 5.86 MPa (850 psi). These conditions were maintained until the rate of hydrogen uptake from the ballast tank fell below 0.0034 MPa/min (0.5 psi/min). The reactor was cooled to room temperature and depressurized, and the reaction product was filtered to remove the catalyst. Solvent was then removed by rotary evaporation. The resulting reaction product was methylamine-terminated poly-(N-methylazacycloheptane) with an estimated amine hydrogen equivalent weight (AHEW) of about 121. The M$_n$ was determined to be approximately 184 using the GC technique described above. Methylamine-terminated poly-(N-methylazacycloheptane) has the following chemical structure:

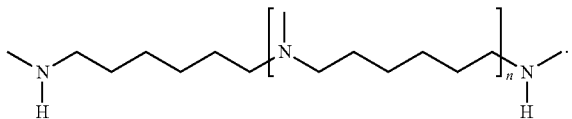

The methylamine-terminated poly-(N-methylazacycloheptane) compound of Example 1 is designated as dimethyl secondary diamine 1, abbreviated DSD-1. DSD-1 was analyzed using gas chromatography (GC) and had the following polymer distribution by area percent, with "others" representing reaction by-products which were not separated or identified using GC, nor used in determining M$_n$:

| | |
|---|---|
| n = 0 | 47.6% |
| n = 1 | 35.7% |
| n = 2 | 5.8% |
| Others | 10.9% |

Example 2

Synthesis of Methylamine-Terminated poly-(N-methylazetidine)

282 g of acrylonitrile and 8.5 g of water were placed in a 1-liter stainless-steel batch pressure reactor equipped with a stirrer. The reactor was sealed and subsequently purged with nitrogen to remove any air from the reactor. While stirring the reactor contents, 200 g of methylamine were added to the reactor over a time period of 5 hours. During the addition of the methylamine, the reactor temperature was maintained in range of 55-60° C. This temperature range was then maintained for 1.5 hours after the methylamine addition was complete. The reactor was cooled and the intermediate product removed.

120 g of isopropanol and 7.5 g of Pd/Al$_2$O$_3$ catalyst were placed in a 1-liter stainless-steel batch pressure reactor equipped with a stirrer and 1-liter hydrogen ballast tank. The Pd/Al$_2$O$_3$ catalyst is commercially available from the Johnson-Mathey Corporation. The reactor was sealed and subsequently purged with nitrogen and hydrogen to remove any air from the reactor. While stirring the reactor contents, 90 g of anhydrous methylamine were added to the reactor. The reactor was then pressurized with hydrogen to 5.86 MPa (850 psi), and heated to 120° C. Over a time period of 5 hours, 450 g of the intermediate product described above were added to the reactor. Substantially constant reactor conditions were maintained for approximately 2 more hours after the addition of the intermediate product was complete, at which time the rate of hydrogen uptake from the ballast tank fell below 0.0034 MPa/min (about 0.5 psi/min). The reactor was cooled to room temperature and depressurized, and the reaction product was filtered to remove the catalyst. The solvent was then removed by rotary evaporation. The resulting reaction product was methylamine-terminated poly-(N-methylazetidine) with an estimated AHEW of about 100. The M$_n$ was determined to be approximately 198 using the GC technique described above. Methylamine-terminated poly-(N-methylazetidine) has the following chemical structure:

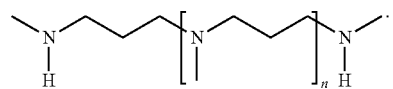

The methylamine-terminated poly-(N-methylazetidine) compound of Example 2 is designated as dimethyl secondary diamine 2, abbreviated DSD-2. DSD-2 was analyzed using GC and had the following polymer distribution by area percent, with "others" representing reaction by-products which were not separated or identified using GC, nor used in determining $M_n$:

|       |       |
|-------|-------|
| n = 0 | 12.6% |
| n = 1 | 26.1% |
| n = 2 | 25.5% |
| n = 3 | 14.7% |
| n = 4 | 7.3%  |
| n = 5 | 3.5%  |
| Others| 10.3% |

Example 3

Synthesis of Methylamine-Terminated poly-(N-methylazetidine)

282 g of acrylonitrile and 8.5 g of water were placed in a 1-liter stainless-steel batch pressure reactor equipped with a stirrer. The reactor was sealed and subsequently purged with nitrogen to remove any air from the reactor. While stirring the reactor contents, 87 g of methylamine were added to the reactor over a time period of 5 hours. During the addition of the methylamine, the reactor temperature was maintained in range of 55-60° C. This temperature range was then maintained for 1.5 hours after the methylamine addition was complete. The reactor was cooled and the intermediate product removed.

120 g of isopropanol and 7 g of Pd/Al$_2$O$_3$ catalyst were placed in a 1-liter stainless-steel batch pressure reactor equipped with a stirrer and 1-liter hydrogen ballast tank. The Pd/Al$_2$O$_3$ catalyst is commercially available from the Johnson-Mathey Corporation. The reactor was sealed and subsequently purged with nitrogen and hydrogen to remove any air from the reactor. While stirring the reactor contents, about 160 g of anhydrous methylamine were added to the reactor. The reactor was then pressurized with hydrogen to 5.86 MPa (850 psi), and heated to 120° C. Over a time period of 5 hours, 350 g of the intermediate product described above were added to the reactor. Substantially constant reactor conditions were maintained for approximately 2 more hours after the addition of the intermediate product was complete, at which time the rate of hydrogen uptake from the ballast tank fell below 0.0034 MPa/min (0.5 psi/min). The reactor was cooled to room temperature and depressurized, and the reaction product was filtered to remove the catalyst. The solvent was then removed by rotary evaporation. The resulting reaction product was methylamine-terminated poly-(N-methylazetidine) with an estimated AHEW of about 113. The $M_n$ was determined to be approximately 253 using the GC technique described above. Methylamine-terminated poly-(N-methylazetidine) has the following chemical structure:

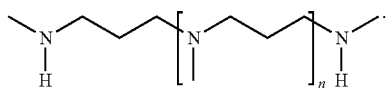

The methylamine-terminated poly-(N-methylazetidine) compound of Example 3 is designated as dimethyl secondary diamine 3, abbreviated DSD-3. DSD-3 was analyzed using GC and had the following polymer distribution by area percent, with "others" representing reaction by-products which were not separated or identified using GC, nor used in determining $M_n$:

|       |       |
|-------|-------|
| n = 0 | 2.8%  |
| n = 1 | 16.6% |
| n = 2 | 18.2% |
| n = 3 | 20.7% |
| n = 4 | 12.2% |
| n = 5 | 9.2%  |
| Others| 20.3% |

Example 4

Synthesis of Methylamine-Terminated poly-(N-methylazetidine)

142.5 parts by weight of acrylonitrile and 3 parts of water were placed in a 1-liter stainless-steel batch pressure reactor equipped with a stirrer. The reactor was sealed and subsequently purged with nitrogen to remove any air from the reactor. While stirring the reactor contents, 100 parts by weight of methylamine were added to the reactor over a time period of 4 hours. During the addition of the methylamine, the reactor temperature was maintained at 55° C. This temperature was then maintained for 1.5 hours after the methylamine addition was complete. The reactor was cooled and the intermediate product removed.

35 parts by weight of isopropanol and 1.5 parts of Pd/Al$_2$O$_3$ catalyst were placed in a 1-liter stainless-steel batch pressure reactor equipped with a stirrer and 1-liter hydrogen ballast tank. The Pd/Al$_2$O$_3$ catalyst is commercially available from the Johnson-Mathey Corporation. The reactor was sealed and subsequently purged with nitrogen and hydrogen to remove any air from the reactor. While stirring the reactor contents, 30 parts by weight of anhydrous methylamine were added to the reactor. The reactor was then pressurized with hydrogen to 5.86 MPa (850 psi), and heated to 120° C. Over a time period of 4 hours, 100 parts by weight of the intermediate product described above were added to the reactor. Substantially constant reactor conditions were maintained for approximately 2 more hours after the addition of the intermediate product was complete, at which time the rate of hydrogen uptake from the ballast tank fell below 0.0034 MPa/min (0.5 psi/min). The reactor was cooled to room temperature and depressurized, and the reaction product was filtered to remove the catalyst. The solvent was then removed by rotary evaporation. The resulting reaction product was methylamine-terminated poly-(N-methylazetidine) with an estimated AHEW of about 117. It had an amine value of 877 mg KOH/g and the Brookfield viscosity was determined to be 17 mPa·s using spindle S62 at 100 rpm. The $M_n$ was determined to be approximately 239 using the GC technique described above. Methylamine-terminated poly-(N-methylazetidine) has the following chemical structure:

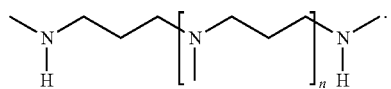

The methylamine-terminated poly-(N-methylazetidine) compound of Example 4 is designated as dimethyl secondary diamine 4, abbreviated DSD-4. DSD-4 was analyzed using GC and had the following polymer distribution by area percent, with "others" representing reaction by-products which were not separated or identified using GC, nor used in determining $M_n$:

| | |
|---|---|
| n = 0 | 7.2% |
| n = 1 | 17.6% |
| n = 2 | 18.2% |
| n = 3 | 15.8% |
| n = 4 | 11.3% |
| n = 5 | 7.9% |
| n = 6 | 4.7% |
| n = 7 | 2.5% |
| Others | 14.8% |

| | |
|---|---|
| n = 0 | 3.4% |
| n = 1 | 11.0% |
| n = 2 | 15.8% |
| n = 3 | 17.0% |
| n = 4 | 12.7% |
| n = 5 | 10.7% |
| n = 6 | 6.7% |
| n = 7 | 0.9% |
| Others | 17.8% |

Example 5

Synthesis of Methylamine-Terminated poly-(N-methylazetidine)

273.5 parts by weight of acrylonitrile and 5.5 parts of water were placed in a 1-liter stainless-steel batch pressure reactor equipped with a stirrer. The reactor was sealed and subsequently purged with nitrogen to remove any air from the reactor. While stirring the reactor contents, 100 parts by weight of methylamine were added to the reactor over a time period of 4 hours. During the addition of the methylamine, the reactor temperature was maintained at approximately 55° C. This temperature was then maintained for 1.5 hours after the methylamine addition was complete. The reactor was cooled and the intermediate product removed.

35 parts by weight of isopropanol and 1.5 parts of $Pd/Al_2O_3$ catalyst were placed in a 1-liter stainless-steel batch pressure reactor equipped with a stirrer and 1-liter hydrogen ballast tank. The $Pd/Al_2O_3$ catalyst is commercially available from the Johnson-Mathey Corporation. The reactor was sealed and subsequently purged with nitrogen and hydrogen to remove any air from the reactor. While stirring the reactor contents, 30 parts by weight of anhydrous methylamine were added to the reactor. The reactor was then pressurized with hydrogen to 5.86 MPa (850 psi), and heated to 120° C. Over a time period of 4 hours, 100 parts by weight of the intermediate product described above were added to the reactor. Substantially constant reactor conditions were maintained for approximately 2 more hours after the addition of the intermediate product was complete, at which time the rate of hydrogen uptake from the ballast tank fell below 0.0034 MPa/min (0.5 psi/min). The reactor was cooled to room temperature and depressurized, and the reaction product was filtered to remove the catalyst. The solvent was then removed by rotary evaporation. The resulting reaction product was methylamine-terminated poly-(N-methylazetidine) with an estimated AHEW of about 113. It had an amine value of 837 mg KOH/g and the Brookfield viscosity was determined to be 21 mPa·s using spindle S62 at 100 rpm. The $M_n$ was determined to be approximately 273 using the GC technique described above. Methylamine-terminated poly-(N-methylazetidine) has the following chemical structure:

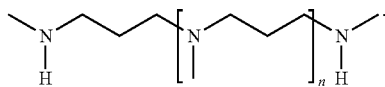

The methylamine-terminated poly-(N-methylazetidine) compound of Example 5 is designated as dimethyl secondary diamine 5, abbreviated DSD-5. DSD-5 was analyzed using GC and had the following polymer distribution by area percent, with "others" representing reaction by-products which were not separated or identified using GC, nor used in determining $M_n$:

Constructive Example 6

Constructive Synthesis of Methylamine-Terminated Polyoxypropylene

The synthesis reaction can be carried out in a continuous reactor such as a stainless steel tube of about 3.175 cm inside diameter and about 69 cm in length. First, place about 487 mL of a pre-reduced, pelletized nickel-copper-chromium catalyst in the reactor. The catalyst can contain approximately 75 mole percent nickel, 23 mole percent copper and 2 mole percent chromium, as described in U.S. Pat. No. 3,654,370, which is incorporated herein by reference. To the reactor contents, add hydrogen at a rate of about 160 liters per hour (measured at 0° C. and 1 atmosphere pressure), methylamine at a rate of about 686 g/hr, and an approximate 50% solution of polypropylene glycol in cyclohexane at a rate of about 304 g/hr. The molecular weight of the polypropylene glycol used in this synthesis can be around 400. The reactor temperature should be controlled at around 240° C., and the pressure maintained at approximately 3000 psig.

The reactor effluent is subsequently stripped of methylamine and cyclohexane by heating to approximately 150° C. The resulting reaction product is a liquid comprising methylamine-terminated polyoxypropylene. The reaction product should have in excess of about 90% of the theoretical content of amino groups, and less than 10% of the original hydroxyl groups. Typically, above about 90% of the amine groups are secondary amino groups resulting in the desired product, methylamine-terminated polyoxypropylene, which is an N,N'-dimethyl secondary diamine polymer. The distribution of molecular sizes and the $M_n$ can then be determined using the GC technique previously described. Additional, the AHEW can be estimated for the methylamine-terminated polyoxypropylene using analytical methods that are well known to those skilled in the art.

Example 7

Synthesis of a Mannich Base Derivative from Methylamine-Terminated poly-(N-methylazetidine) and tris-(dimethylaminomethyl)phenol 50.03 g of the dimethyl secondary diamine of Example 3 (DSD-3) and 26.61 g of K54, tris-(dimethylaminomethyl) phenol, were placed in a round-bottom flask equipped with a nitrogen inlet, mechanical stirrer, thermocouple, and a reflux condenser. The top of the reflux condenser was connected to a Dewar condenser which was attached to the center neck of a second round-bottom flask, which was equipped with a magnetic stir bar and a nitrogen outlet. This second round-bottom flask was charged with 19.87 g of acetic acid and 39.77 g of distilled water.

While stirring, the temperature of the mixture of DSD-3 and K54 was increased from ambient temperature to 190° C. over the course of 2.5 hours, and held at this temperature for an additional 3 hours. Subsequently, the temperature was increased to 200° C. and maintained for 1 hour.

The resulting reaction product was a Mannich base derivative of methylamine-terminated poly-(N-methylazetidine). This composition had a viscosity of 639 mPa·s at 25° C. using Brookfield CP52 spindle at 20 rpm, and an amine value of 831 mg KOH/g. In the tables that follow, this composition of Example 7 is designated as MBC-7.

Example 8

Synthesis of a Mannich Base Derivative from Methylamine-Terminated poly-(N-methylazetidine) and tris-(dimethylaminomethyl)phenol 50.02 g of the dimethyl secondary diamine of Example 4 (DSD-4) and 20.45 g of K54 were placed in a round-bottom flask equipped with a nitrogen inlet, mechanical stirrer, thermocouple, and a reflux condenser. The top of the reflux condenser was connected to a Dewar condenser which was attached to the center neck of a second round-bottom flask, which was equipped with a magnetic stir bar and a nitrogen outlet. This second round-bottom flask was charged with 15.29 g of acetic acid and 30.56 g of distilled water.

While stirring, the temperature of the mixture of DSD-4 and K54 was increased from ambient temperature to 160° C. over the course of 20 minutes, and held at this temperature for an additional 3 hours. Subsequently, the temperature was increased to 180° C. for 2 hours, then increased to 200° C. for additional 2 hours.

The resulting reaction product was a Mannich base derivative of methylamine-terminated poly-(N-methylazetidine). This composition had a viscosity of 2614 mPa·s at 25° C. using Brookfield CP52 spindle at 20 rpm, and an amine value of 820 mg KOH/g. In the tables that follow, this composition of Example 8 is designated as MBC-8.

Example 9

Synthesis of a Mannich Base Derivative from Methylamine-Terminated poly-(N-methylazetidine) and tris-(dimethylaminomethyl)phenol 50.05 g of the dimethyl secondary diamine of Example 4 (DSD-4) and 17.72 g of K54 were placed in a round-bottom flask equipped with a nitrogen inlet, mechanical stirrer, thermocouple, and a reflux condenser. The top of the reflux condenser was connected to a Dewar condenser which was attached to the center neck of a second round-bottom flask, which was equipped with a magnetic stir bar and a nitrogen outlet. This second round-bottom flask was charged with 13.27 g of acetic acid and 26.5 g of distilled water.

While stirring, the temperature of the mixture of DSD-4 and K54 was increased from ambient temperature to 200° C. over the course of 3 hours, and maintained at this temperature for an additional 3 hours.

The resulting reaction product was a Mannich base derivative of methylamine-terminated poly-(N-methylazetidine). This composition had a viscosity of 59 mPa·s at 25° C. using Brookfield CP52 spindle at 20 rpm, and an amine value of 850 mg KOH/g. In the tables that follow, this composition of Example 9 is designated as MBC-9.

Example 10

Synthesis of a Mannich Base Derivative from Methylamine-Terminated poly-(N-methylazetidine) and tris-(dimethylaminomethyl)phenol 46.75 g of the dimethyl secondary diamine of Example 4 (DSD-4) and 12.74 g of K54 were placed in a round-bottom flask equipped with a nitrogen inlet, mechanical stirrer, thermocouple, and a reflux condenser. The top of the reflux condenser was connected to a Dewar condenser which was attached to the center neck of a second round-bottom flask, which was equipped with a magnetic stir bar and a nitrogen outlet. This second round-bottom flask was charged with 9.54 g of acetic acid and 19.04 g of distilled water.

While stirring, the temperature of the mixture of DSD-4 and K54 was increased from ambient temperature to 160° C. over the course of 20 minutes, and held at this temperature for an additional 1 hour. Subsequently, the temperature was increased to 178° C. and maintained for 30 minutes, then increased to 187° C. and maintained for 1 hour, and then increased to 195° C. and maintained for 2 hours.

The residual methylamine-terminated poly-(N-methylazetidine) reactant in the system was estimated by GC, using diglyme as an internal standard, and measuring the amount of the n=1 and n=2 oligomers before and after completion of the reaction. The average of the two measurements indicated that the final product incorporated approximately 44% of the weight of the methylamine-terminated poly-(N-methylazetidine) reactant based on the weight of DSD-4 charged in the initial reaction mixture.

Comparative Examples 11-12

Coatings Made from Comparative Epoxy-Hardener Compositions

Formulations and the resulting properties of comparative examples 11-12 are illustrated in Tables 2-3. As indicated in the tables, the coatings based on the phenalkamines of Examples 11-12 had slow dry speeds at 5° C., particularly as measured by the thumb twist method. Additionally, the coatings of Examples 11-12 exhibited poor hardness development, waterspot resistance, reverse impact and mandrel bend flexibility.

TABLE 2

Comparative examples cured at 25° C. or following cure schedules A-C.

| | Example | |
| --- | --- | --- |
| | 11 | 12 |
| Comparative Hardener | NC541LV | CX-105 |
| Use Level (PHR) | 67 | 76 |
| Mix Viscosity (mPa · s) | 6,250 | 22,000 |
| Coating Solids (weight %) | | |
| At mix viscosity | 100 | 100 |
| Diluted to 1 Pa · s$^a$ | 94 | 87 |
| Thin Film Set Time (hr) | | |
| Phase 2/Phase 3 | 4.6/5.8 | —/— |
| Coating Appearance | | |
| Specular Gloss 20°/60° | 82/92 | 10/50 |
| Visual | glossy | semi gloss |
| Persoz Hardness (s) | | |
| Day 1/Day 7 | 165/275 | 90/190 |
| Impact Resistance (kg · cm) | | |

TABLE 2-continued

Comparative examples cured at 25° C. or following cure schedules A-C.

| | Example | |
|---|---|---|
| | 11 | 12 |
| Direct/Reverse | | |
| Schedule A | 125/20 | 85/17 |
| Schedule B | 115/45 | |
| Schedule C | | |
| Mandrel Bend (% elongat.) | | |
| Schedule A | 5.2 | 5.3 |
| Conical Bend (% elongat.) | | |
| Schedule A | <2 | <2 |

<sup>a</sup>adjusted with xylene:butanol (3:1) to match comparable application viscosity

TABLE 3

Comparative examples cured at 5° C.

| | Example | |
|---|---|---|
| | 11 | 12 |
| Thin Film Set Time (hr) | | |
| Phase 2/Phase 3 | 14/20 | 9.7/15.2 |
| Coating Appearance | | |
| Specular Gloss 20°/60° | 40/80 | 12/34 |
| Visual | greasy | Matte |
| Persoz Hardness (s) | | |
| Day 2/Day 7 | —/115 | 25/75 |

TABLE 3-continued

Comparative examples cured at 5° C.

| | Example | |
|---|---|---|
| | 11 | 12 |
| Thumb Twist method | | |
| Set-to-Touch Time (hr) | 22 | 24 |
| Dry-to-Handle Time (hr) | 26 | >28 |
| Waterspot Resistance | | |
| Day 1/Day 7 (1-5, 5 = best) | 1/3 | 2/3 |

Examples 13-17

Coatings Made from Amine-Epoxy Compositions

Formulations and the resulting properties of inventive examples 13-17 are shown in Tables 4-5. Examples 13-17 illustrate the properties obtained from exemplary formulations and coatings utilizing compositions containing Mannich base derivatives of N,N'-dimethyl secondary diamines in accordance with the present invention.

As indicated in Table 4, Examples 13, 14, and 16, utilized MBC-7, MBC-8, and MBC-9, respectively, with a multifunctional amine, MPCA. Example 15 did not contain benzyl alcohol. Example 17 contained MBC-9 and a derivative of a multifunctional amine (phenalkamine).

As illustrated by Tables 2 and 4, the coatings of Examples 13-17 exhibited higher gloss, and superior flexibility and impact resistance, as compared to Examples 11-12. The data in Tables 3 and 5 at 5° C. demonstrate the generally improved gloss and faster dry speed of the coatings of Examples 13-17 versus those of Examples 11-12. Tables 2-5 also show the significantly increased Persoz hardness for the coatings of Examples 13-17 over the comparable coatings of Examples 11-12. Example 15 additionally demonstrates that Mannich base derivatives of the present invention can be used as sole curatives to yield 100% solids formulations with generally good coating properties.

TABLE 4

Examples 13-17 cured at 25° C. or following cure schedules A-C.

| | Example | | | | | | | | | |
|---|---|---|---|---|---|---|---|---|---|---|
| | 13 | | 14 | | 15 | | 16 | | 17 | |
| Hardener Composition (Parts by Weight) | MBC-7 | 75 | MBC-8 | 75 | MBC-9 | 100 | MBC-9 | 75 | MBC-9 | 50 |
| | MPCA | 25 | MPCA | 25 | | | MPCA | 25 | CX-105 | 50 |
| | BA | 42 | BA | 36 | | | BA | 42 | | |
| Use Level (PHR) with DGEBA | 84 | | 91 | | 94 | | 86 | | 83 | |
| Mix Viscosity (mPa·s) | 2,700 | | 4,800 | | 4,000 | | 1,900 | | 8,800 | |
| Coating Solids (weight %) | 86 | | 87 | | 100 | | 86 | | 100 | |
| Thin Film Set Time (hr) | | | | | | | | | | |
| Phase 2/Phase 3 | 2.4/3.1 | | 1.8/2.8 | | —/— | | —/— | | —/— | |
| Coating Appearance | | | | | | | | | | |
| Specular Gloss 20°/60° | 100/101 | | 99/101 | | >95 | | >95 | | >95 | |
| Visual | high gloss | | high gloss | | high gloss | | high gloss | | high gloss | |
| Persoz Hardness (s) | | | | | | | | | | |
| Day 1/Day 7 | 315/325 | | 305/320 | | 305/280 | | 280/285 | | 315/325 | |
| Impact Resistance (kg·cm) Direct/Reverse | | | | | | | | | | |
| Schedule A | 120/40 | | 185/35 | | 200/200 | | 170/85 | | 140/35 | |
| Schedule B | 200/175 | | 200/200 | | | | | | | |
| Schedule C | 165/30 | | 150/20 | | | | | | | |

TABLE 4-continued

Examples 13-17 cured at 25° C. or following cure schedules A-C.

| | Example | | | | |
|---|---|---|---|---|---|
| | 13 | 14 | 15 | 16 | 17 |
| Mandrel Bend (% elongat.) | | | | | |
| Schedule A | 33 | — | 33 | 33 | 5.3 |
| Conical Bend (% elongat.) | | | | | |
| Schedule A | >33 | — | >33 | >33 | 4.4 |

[a] adjusted with xylene:butanol (3:1) to match comparable application viscosity

TABLE 5

Examples 13-17 cured at 5° C.

| | Example | | | | |
|---|---|---|---|---|---|
| | 13 | 14 | 15 | 16 | 17 |
| Thin Film Set Time (hr) | | | | | |
| Phase 2/Phase 3 Thumb Twist method | 7.4/10.0 | 6.6/11.0 | 7.0/— | 6.5/9.0 | 9.0/12.6 |
| Set-to-Touch Time (hr) | — | — | — | 8 | 9 |
| Dry-to-Handle Time (hr) | <16 | <16 | <22 | 9 | 10 |
| Coating Appearance | | | | | |
| Specular Gloss 20°/60° | 29/53 | 58/84 | 40/73 | 97/100 | 81/94 |
| Visual | semi-gloss | semi-gloss | semi-gloss | high gloss | glossy |
| Waterspot Resistance | | | | | |
| Day 1/Day 7 (1-5, 5 = best) | 5/5 | —/— | 2/3 | 5/5 | 4/5 |
| Persoz Hardness (s) | | | | | |
| Day 1/Day 7 | 95/240 | 80/215 | 45/85 | 75/180 | 135/250 |

Examples 18-25

Synthesis of Mannich Base Derivatives from Methylamine-Terminated poly-(N-methylazetidine), phenol, and formaldehyde Phenol and the dimethyl secondary diamine of Example 4 (DSD-4) were placed in a 4-necked reaction flask equipped with a nitrogen purge, mechanical stirrer, thermocouples, and reflux condenser, at the quantities and conditions listed in Table 6. Reaction temperature and the head temperature at the take-off point of the condenser were monitored using the thermocouples.

The general procedure for each of Examples 18-25 was as follows. A formaldehyde solution (37% in water and methanol) was added slowly at room temperature over a 20-30 minute period to the reaction flask, keeping the exothermic reaction to a minimum. Once addition of the formaldehyde was complete, a sample was taken for GC analysis of free phenol as an indicator of the progress of the reaction. The temperature was then increased to the desired temperature (70 or 90° C.) and held at that temperature for about 6 hours as methanol and water were removed from the reaction mixture. The reaction mixture was sampled hourly for free phenol by GC. Total reaction times were generally about 6.5 to 7 hours.

Methanol and water were then removed by distillation, accomplished by heating the reaction product to 115° C. and allowing the distillate to travel through a 28 mm distillation column (available from Ace Glass catalog #6566-03) into a condenser cooled to 12° C. Once the head temperature started to drop after the distillate had been collected, the pot temperature was increased in 10° C. increments and the distillation step repeated. Generally, three distillation cuts were necessary to strip the final reaction product of water to less than 1-2% water.

Table 7 summarizes the characterization of the final reaction products of Examples 18-25. The free phenol in all products was less than 2%, and in most cases, the free phenol was less than 0.5%. Hence, Mannich base derivatives of a N,N'-dimethyl secondary amine polymer with very low levels of residual phenol can be prepared by the direct reaction of phenol, formaldehyde, and a N,N'-dimethyl secondary amine polymer, such as methylamine-terminated poly-(N-methylazetidine).

TABLE 6

Experimental Conditions for Examples 18-25.

| Example | $CH_2O$/Phenol Mole Ratio | DSD-4/Phenol Mole Ratio | DSD-4 (g) | Phenol (g) | 37% $CH_2O$ (g) | Reaction Temp. (° C.) |
|---|---|---|---|---|---|---|
| 18 | 2.6 | 3.5 | 225.07 | 25.96 | 58.19 | 70 |
| 19 | 2.9 | 3.5 | 225.08 | 25.98 | 64.99 | 70 |
| 20 | 2.6 | 4.5 | 233.26 | 20.88 | 46.91 | 70 |
| 21 | 2.9 | 4.5 | 233.21 | 20.94 | 52.13 | 70 |
| 22 | 2.6 | 3.5 | 225.33 | 26.23 | 58.95 | 90 |
| 23 | 2.9 | 3.5 | 225.24 | 26.56 | 64.87 | 90 |
| 24 | 2.6 | 4.5 | 231.26 | 20.86 | 47.20 | 90 |
| 25 | 2.9 | 4.5 | 233.33 | 20.99 | 52.36 | 90 |

TABLE 7

Characterization of Mannich base derivatives of Examples 18-25.

| Example | Final Yield (g) | Calculated AHEW | % Water (K. F.) | % Phenol | Viscosity (mPa · s, 25° C.) |
|---|---|---|---|---|---|
| 18 | 226.75 | 188 | 1.7 | 0.37 | 309 |
| 19 | 216.88 | 193 | 2.0 | 0.09 | 704 |
| 20 | 217.14 | 153 | 1.5 | 1.54 | 94 |
| 21 | 218.24 | 162 | 1.0 | 0.72 | 132 |
| 22 | 212.56 | 177 | 1.4 | 0.06 | 688 |
| 23 | 200.00 | 178 | 1.4 | 0.07 | 724 |
| 24 | 225.94 | 162 | 0.5 | 0.15 | 106 |
| 25 | 225.81 | 167 | 1.3 | 0.06 | 157 |

Note
% Water (K. F.) indicates measurement by Karl Fischer titration

Example 26

Synthesis of a Mannich Base Derivative from Methylamine-Terminated poly-(N-methylazetidine) and tris-(dimethylaminomethyl)phenol 2585.1 g of the dimethyl secondary diamine of Example 4 (DSD-4) and 918.9 g of K54 were placed in a round-bottom flask equipped with a nitrogen inlet, mechanical stirrer, thermocouple, and a reflux condenser. The top of the reflux condenser was connected to a Dewar condenser which was attached to the center neck of a second round-bottom flask, which was equipped with a magnetic stir bar and a nitrogen outlet. This second round-bottom flask was charged with 684.4 g of acetic acid and 1368.6 g of distilled water.

While stirring, the temperature of the mixture of DSD-4 and K54 was increased from ambient temperature to 150° C. over the course of 114 minutes, and held at this temperature for an additional 7.75 hours.

The resulting reaction product was a Mannich base derivative of methylamine-terminated poly-(N-methylazetidine). This composition had a viscosity of 2945 mPa·s at 25° C. using Brookfield CP52 spindle at 20 rpm, and an amine value of 762 mg KOH/g. The calculated AHEW for this composition was 249.

Examples 27-35

Coatings Made from Amine-Epoxy Compositions

Formulations and the resulting properties of Examples 27-35 are summarized in Table 8. In accordance with the present invention, Examples 27-35 illustrate the properties obtained from exemplary formulations and coatings utilizing compositions containing Mannich base derivatives of N,N'-dimethyl secondary diamines and a multifunctional amine.

Hardeners for these experiments were prepared by mixing 50 parts by weight of the Mannich base derivatives of Examples 18-26 with 50 parts by weight of CX-105. The resulting amine curing agent compositions were then contacted and mixed with the epoxy resin, and coated and tested as described above. For Examples 27-34, the stoichiometric ratio of epoxy groups in the epoxy resin to amine hydrogens in the amine curing agent composition (hardener composition) was about 1:1. The AHEW of the respective Mannich base derivative of Examples 18-26 provided above was used in this determination. The AHEW in Table 8 is that of the amine curing agent composition or hardener composition, i.e., CX-105 mixed with the respective Mannich base derivative. The epoxy:amine stoichiometric ratio for Example 35 was about 1.18:1.

As compared to the coatings of Examples 11-12 cured at 5° C. (see Table 3), the coatings of Examples 27-35 generally show an improvement in drying time (phase 2 thin film set time) and 200 gloss. In addition, 7 day Persoz hardness is increased dramatically for Examples 27-28, 31-32, and 35.

TABLE 8

Examples 27-35 cured at 5° C. and 60% RH.

| | | Example | | | | | | | | |
|---|---|---|---|---|---|---|---|---|---|---|
| | | 27 | 28 | 29 | 30 | 31 | 32 | 33 | 34 | 35 |
| Hardener Example | | 18 | 19 | 20 | 21 | 22 | 23 | 24 | 25 | 26 |
| AHEW | | 165 | 168 | 147 | 151 | 159 | 159 | 151 | 154 | 156 |
| Persoz Hardness | Day 1 | 40 | 45 | 30 | 30 | 25 | 30 | 30 | 25 | 130 |
| | Day 3 | 150 | 145 | 75 | 60 | 80 | 130 | 65 | 55 | 220 |
| | Day 7 | 235 | 190 | 105 | 80 | 215 | 210 | 75 | 100 | 250 |
| Gloss | 20° | 35 | 40 | 30 | 30 | 75 | 45 | 60 | 35 | 75 |
| Thin Film Set Time (hr) | [I] | 3.7 | 4.0 | 3.8 | 4.1 | 4.3 | 3.3 | 3.5 | 3.5 | 3.5 |
| | [II] | 9.0 | 9.9 | 9.8 | 9.6 | 9.2 | 8.5 | 8.7 | 8.7 | 7.7 |

Examples 36-41

Impact of the Stoichiometric Ratio of Epoxy Groups to Amine Hydrogens on Coating Properties Formulations and the resulting properties of inventive Examples 36-41 are summarized in Table 9. In accordance with the present invention, Examples 36-41 illustrate the effect of changing the stoichiometric ratio of epoxy groups in the epoxy component to amine hydrogens in the amine component. The amine component was prepared by mixing 75 parts by weight of Example 26 (Mannich base derivative of methylamine-terminated poly-(N-methylazetidine) having an AHEW of about 249), 25 parts MPCA having an AHEW of about 57, and 44 parts benzyl alcohol. The resulting amine curing agent compositions were then contacted and mixed with the epoxy resin at the stoichiometric ratio indicated, and coated and tested as described above.

Examples 36-41 demonstrate that improved hardness and gloss result when excess epoxy is employed. In this set of examples, optimum properties were obtained with a stoichiometric ratio of epoxy to amine of about 1.16:1 in Example 40.

TABLE 9

Examples 36-41 cured at 5° C. and 60% RH.

| | Example | | | | | |
|---|---|---|---|---|---|---|
| | 36 | 37 | 38 | 39 | 40 | 41 |
| Stoichiometry | | | | | | |
| Epoxy:Amine Groups | 1:1.04 | 1:1 | 1.04:1 | 1.09:1 | 1.16:1 | 1.25:1 |
| AHEW of blend | 198 | 191 | 183 | 174 | 163 | 151 |
| Use Level (PHR) | 104 | 100 | 96 | 92 | 86 | 80 |
| Persoz Hardness | | | | | | |
| Day 2 | 75 | 95 | 110 | 135 | 150 | 130 |
| Gloss-20° | 55 | 65 | 80 | 85 | 95 | 80 |
| Gloss-60° | 85 | 90 | 95 | 105 | 110 | 95 |
| Thin Film Set Time (hr) | | | | | | |
| Phase 2 | 4.7 | 4.7 | 4.8 | 4.8 | 4.8 | 4.8 |

We claim:

1. An epoxy curing agent composition comprising: Mannich base derivatives of an N,N'-dimethyl secondary diamine polymer comprising the contact product of
   (a) at least one aldehyde compound;
   (b) at least one phenol compound; and
   (c) at least one N,N'-dimethyl secondary diamine polymer having a number-average molecular weight ($M_a$) from about 140 to about 1000; and said Mannich base derivatives of an N,N'-dimethyl secondary diamine polymer having the formula:

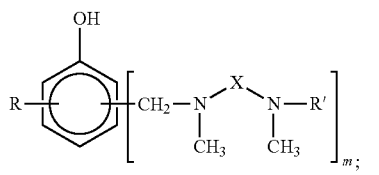

(I-A)

wherein:
  m is 1, 2, or 3;
    R is a hydrogen atom or a $C_1$-$C_{18}$ linear or branched alkyl or alkenyl group;
    each R' independently is a hydrogen atom or a moiety having the formula:

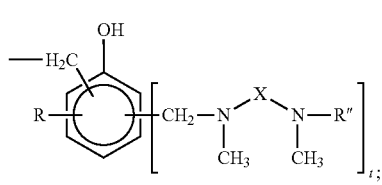

(I-B)

wherein:
  R is defined as above;
  t is 1 or 2 ;
  each R" independently is a hydrogen atom or a moiety having the formula;

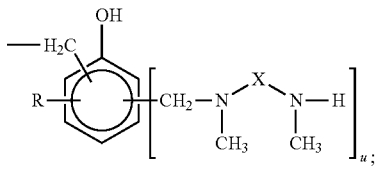

(I-C)

wherein:
  R is defined as above;
  u is 0, 1, or 2; and
  each X independently is a polyoxyalkylene moiety or a moiety having the formula:

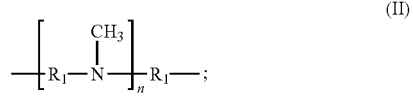

(II)

wherein:
  R1 is a C2-C8 linear or branched alkanediyl; and
  n is an integer in a range from 1 to 10, inclusive;
and wherein:
  the at least one aldehyde compound comprises formaldehyde;
  the at least one phenol compound comprises phenol, cresol, t-butyl phenol, nonyl phenol, cardanol, or a combination thereof; and
  the at least one N,N'-dimethyl secondary diamine polymer comprises methylamine-terminated poly-(N-methylazetidine), methylamine-terminated poly-(N-methylazacycloheptane), or a combination thereof.

2. The composition of claim 1 wherein the phenol compound comprises phenol.

3. The composition of claim 1 wherein u is 1 or 2.

4. An epoxy curing agent composition comprising: Mannich base derivatives of an N,N'-dimethyl secondary diamine polymer comprising the contact product of
   (d) at least one aldehyde compound;
   (e) at least one phenol compound; and
   (f) at least one N,N'-dimethyl secondary diamine polymer having a number-average molecular weight ($M_a$) from about 140 to about 1000; and said Mannich base derivatives of an N,N'-dimethyl secondary diamine polymer having the formula:

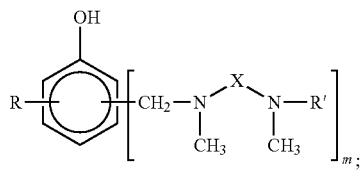

(I-A)

wherein:
  m is 1, 2, or 3;
    R is a hydrogen atom or a $C_1$-$C_{18}$ linear or branched alkyl or alkenyl group;
    each R' is a hydrogen atom; and
    each X independently is a polyoxyalkylene moiety or a moiety having the formula:

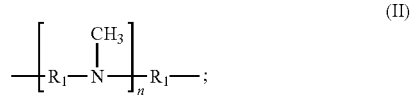

(II)

wherein:
R1 is a C2-C8 linear or branched alkanediyl; and
n is an integer in a range from 1 to 10, inclusive.

5. The composition of claim 4, wherein R is a hydrogen atom, a methyl group, an ethyl group, a propyl group, a butyl group, a tert-butyl group, an octyl group, a nonyl group, a dodecyl group, a C15 alkyl group, or a C15 alkenyl group.

6. An amine curing agent composition comprising:
(i) the composition of claim 4; and
(ii) at least one multifunctional amine having 3 or more active amine hydrogens.

7. An amine-epoxy composition comprising:
(a) the amine curing agent composition of claim 6;
(b) and
an epoxy component comprising at least one multifunctional epoxy resin.

8. A method comprising curing the amine-epoxy composition of claim 7.

9. A composition obtained by the method of claim 8.

10. An article of manufacture comprising the composition of claim 9, wherein the article is a coating, an adhesive, a construction product, a flooring product, or a composite product.

11. The composition of claim 7 wherein the composition is curable at a temperature of less than about 23° C.

12. The composition of claim 6 wherein the multifunctional amine has at least 6 carbon atoms.

13. The amine curing agent composition of claim 6 wherein the amine curing agent composition comprises about 25 to about 75% of the composition of claim 4.

14. The composition of claim 4 further comprising at least one diluent or solvent.

15. The composition of claim 14 wherein the diluent or solvent comprises benzyl alcohol.

16. The composition of claim 4, wherein the composition comprises less than 2% free phenol compound.

17. The composition of claim 4, wherein the composition comprises less than 0.5% free phenol compound.

18. The composition of claim 4 wherein the composition has an amine hydrogen equivalent weight of about 105 to about 500.

19. An epoxy curing agent composition comprising: Mannich base derivatives of an N,N'-dimethyl secondary diamine polymer comprising the contact product of
(a) at least one aldehyde compound;
(b) at least one phenol compound; and
(c) at least one N,N'-dimethyl secondary diamine polymer having a number-average molecular weight ($M_a$) from about 140 to about 1000; and said Mannich base derivatives of an N,N'-dimethyl secondary diamine polymer having the formula:

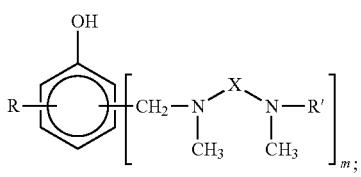

(I-A)

wherein:
m is 1, 2, or 3;
R is a hydrogen atom or a $C_1$-$C_{18}$ linear or branched alkyl or alkenyl group;
each R' independently is a hydrogen atom or a moiety having the formula:

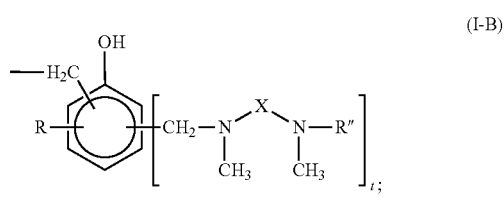

(I-B)

wherein:
R is defined as above;
t is 1 or 2;
each R" independently is a hydrogen atom or a moiety having the formula;

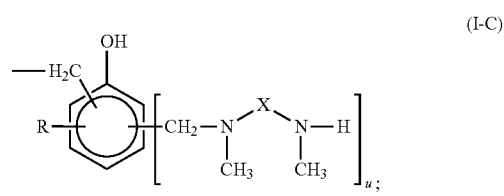

(I-C)

wherein:
R is defined as above;
u is 0, 1, or 2; and
wherein X is a moiety having the formula:

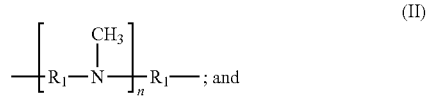

(II)

wherein R1 is a C3-C6 linear or branched alkanediyl and n is an integer in a range of 1 to 50, inclusive.

20. The epoxy curing agent composition of claim 19 wherein the composition has an amine value of about 85 to about 910 mg KOH/g.

21. The epoxy curing agent composition of claim 19 wherein the contact product comprises a liquid polymer and the amine hydrogen equivalent weight of the contact product is effective to cure, harden or crosslink a multifunctional epoxy resin.

22. A composition comprising the contact product of:
formaldehyde;
at least one member selected from the group consisting of phenol and cardanol; and
poly-(N-methyl-azetidine); wherein the composition comprises a polymeric secondary methylamine terminated Mannich base.

* * * * *